United States Patent
Hammershøj et al.

(10) Patent No.: US 11,801,324 B2
(45) Date of Patent: Oct. 31, 2023

(54) METHOD FOR PREPARING A HAEMOSTATIC COMPOSITION

(71) Applicants: Ferrosan Medical Devices A/S, Søborg (DK); Ethicon Inc., Somerville, NJ (US)

(72) Inventors: Peter Lund Hammershøj, Brønshøj (DK); Kristian Larsen, Værløse (DK); Douglas B. Johns, Milford, NJ (US); Nicole Smith, Hoboken, NJ (US); Michael Cardinale, Morristown, NJ (US); Gabriella Ferrara, Old Tappan, NJ (US); Guanghui Zhang, Belle Mead, NJ (US)

(73) Assignees: Ferrosan Medical Devices A/S, Søborg (DK); Ethicon Inc., Somerville, NJ (US)

( * ) Notice: Subject to any disclaimer, the term of this patent is extended or adjusted under 35 U.S.C. 154(b) by 154 days.

(21) Appl. No.: 16/407,503

(22) Filed: May 9, 2019

(65) Prior Publication Data

US 2019/0343981 A1    Nov. 14, 2019

Related U.S. Application Data

(60) Provisional application No. 62/669,056, filed on May 9, 2018.

(51) Int. Cl.
*A61L 24/04* (2006.01)
*A61B 17/12* (2006.01)
*A61L 24/00* (2006.01)
*A61B 17/00* (2006.01)

(52) U.S. Cl.
CPC ...... *A61L 24/043* (2013.01); *A61B 17/12186* (2013.01); *A61L 24/0042* (2013.01); *A61B 2017/00495* (2013.01); *A61L 2400/04* (2013.01); *A61L 2400/06* (2013.01)

(58) Field of Classification Search
CPC ............ A61L 24/043; A61L 24/0042; A61L 2400/04; A61L 2400/06; A61L 15/64; A61L 15/32; A61L 15/44; A61L 24/104; A61L 2300/254; A61L 2300/418; A61B 17/12186; A61B 2017/00495; A61B 17/00491; A61J 1/2089
See application file for complete search history.

(56) References Cited

U.S. PATENT DOCUMENTS

| | | | |
|---|---|---|---|
| 2,465,357 A | 3/1949 | Correll et al. |
| 2,465,860 A | 3/1949 | Fleischmann |
| 2,507,244 A | 5/1950 | Correll |
| 2,558,395 A | 6/1951 | Studer |
| 2,899,362 A | 8/1959 | Sieger et al. |
| 3,089,815 A | 5/1963 | Kupelwieser et al. |
| 3,224,434 A | 12/1965 | Molomut et al. |
| 3,514,518 A | 5/1970 | Charier-Vadrot |
| 3,608,593 A | 9/1971 | McCormick et al. |
| 3,815,580 A | 6/1974 | Oster |
| 3,869,539 A | 3/1975 | Kring et al. |
| 3,892,876 A | 7/1975 | Hobday et al. |
| 3,930,052 A | 12/1975 | De Brou et al. |
| 3,946,732 A | 3/1976 | Hurscham |
| 4,002,173 A | 1/1977 | Manning et al. |
| 4,006,220 A | 2/1977 | Gottlieb |
| 4,013,078 A | 3/1977 | Feild |
| 4,098,728 A | 7/1978 | Rosenblatt et al. |
| 4,107,288 A | 8/1978 | Oppenheim et al. |
| 4,124,705 A | 11/1978 | Rothman et al. |
| 4,150,744 A | 4/1979 | Fennimore |
| 4,160,022 A | 7/1979 | Delaney et al. |
| 4,164,559 A | 8/1979 | Miyata et al. |
| 4,179,400 A | 12/1979 | Tsao et al. |
| 4,194,392 A | 3/1980 | Lombard et al. |
| 4,208,439 A | 6/1980 | Hsu |
| 4,256,877 A | 3/1981 | Karlsson et al. |
| 4,265,233 A | 5/1981 | Sugitachi et al. |
| 4,280,954 A | 7/1981 | Yannas et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,320,201 A | 3/1982 | Berg et al. |
| 4,347,234 A | 8/1982 | Wahlig |
| 4,362,567 A | 12/1982 | Schwarz et al. |

(Continued)

FOREIGN PATENT DOCUMENTS

| | | |
|---|---|---|
| BG | 0051589 | 7/1993 |
| BG | 0099900 | 3/1997 |

(Continued)

OTHER PUBLICATIONS

Surgiflo Haemostatic Matrix Kit. European Medicines Agency, pp. 1-28. (Year: 2012).*

"Formulation and Evaluation of Absorbable Gelatin Sponges," Chapter 3A of Rupali Kale thesis: Design and Development of Surgical Dressings for Advanced Wound Management (2010).

(Continued)

*Primary Examiner* — Jessica Worsham

(74) *Attorney, Agent, or Firm* — Hamilton, Brook, Smith & Reynolds, P.C.

(57) ABSTRACT

The present disclosure relates to a method for preparing a haemostatic composition comprising thrombin, the method comprising the step of reconstituting a dry thrombin directly in a paste, such as a paste comprising a biocompatible polymer. The haemostatic composition comprising thrombin may be prepared from a dry thrombin composition and a paste in a single step operation and be used for treatment of a wound.

18 Claims, 3 Drawing Sheets

(56) References Cited

U.S. PATENT DOCUMENTS

| | | |
|---|---|---|
| 4,377,572 A | 3/1983 | Schwarz et al. |
| 4,416,813 A | 11/1983 | Ikeda et al. |
| 4,424,208 A | 1/1984 | Wallace et al. |
| 4,453,939 A | 6/1984 | Zimmerman |
| 4,482,386 A | 11/1984 | Wittwer et al. |
| 4,492,305 A | 1/1985 | Avery |
| 4,515,637 A | 5/1985 | Cioca |
| 4,522,302 A | 6/1985 | Paikoff |
| 4,536,387 A | 8/1985 | Sakamoto et al. |
| 4,540,410 A | 9/1985 | Wood et al. |
| 4,543,332 A | 9/1985 | Jao et al. |
| 4,549,554 A | 10/1985 | Markham |
| 4,554,156 A | 11/1985 | Fischer |
| 4,556,156 A | 12/1985 | Frutin |
| 4,557,377 A | 12/1985 | Maloney |
| 4,559,304 A | 12/1985 | Kasai et al. |
| 4,600,574 A | 7/1986 | Lindner et al. |
| 4,640,834 A | 2/1987 | Eibl et al. |
| 4,655,211 A | 4/1987 | Sakamoto et al. |
| 4,685,597 A | 8/1987 | Hirao et al. |
| 4,696,812 A | 9/1987 | Silbering |
| 4,702,737 A | 10/1987 | Pizzino |
| 4,735,616 A | 4/1988 | Eibl et al. |
| 4,743,229 A | 5/1988 | Chu |
| 4,746,514 A | 5/1988 | Warne |
| 4,749,689 A | 6/1988 | Miyata et al. |
| 4,752,466 A | 6/1988 | Saferstein et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,885,161 A | 12/1989 | Cornell |
| 4,887,743 A | 12/1989 | Blake et al. |
| 4,891,359 A | 1/1990 | Saferstein et al. |
| 4,920,158 A | 4/1990 | Murray et al. |
| 4,925,677 A | 5/1990 | Feijen |
| 4,936,835 A | 6/1990 | Haaga et al. |
| 4,946,870 A | 8/1990 | Partain, III et al. |
| 4,965,203 A | 10/1990 | Silbering et al. |
| 4,982,769 A | 1/1991 | Fournier et al. |
| 4,997,753 A | 3/1991 | Dean, Jr. et al. |
| 5,007,916 A | 4/1991 | Linsky et al. |
| 5,017,229 A | 5/1991 | Burns et al. |
| 5,023,082 A | 6/1991 | Friedman et al. |
| 5,024,841 A | 6/1991 | Chu et al. |
| 5,037,740 A | 8/1991 | Tanaka et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,112,750 A | 5/1992 | Tanaka et al. |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,180,583 A | 1/1993 | Hedner |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,281,528 A | 1/1994 | Boctor et al. |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,350,581 A | 9/1994 | Kochinke |
| 5,352,715 A | 10/1994 | Wallace et al. |
| 5,356,614 A | 10/1994 | Sharma |
| 5,356,883 A | 10/1994 | Kuo et al. |
| 5,384,333 A | 1/1995 | Davis et al. |
| 5,385,606 A | 1/1995 | Kowanko |
| 5,387,208 A | 2/1995 | Ashton et al. |
| 5,394,886 A | 3/1995 | Nabai et al. |
| 5,397,704 A | 3/1995 | Boctor et al. |
| 5,399,361 A | 3/1995 | Song et al. |
| 5,401,511 A | 3/1995 | Margalit |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,441,491 A | 8/1995 | Verschoor et al. |
| 5,443,481 A | 8/1995 | Lee |
| 5,447,966 A | 9/1995 | Hermes et al. |
| 5,456,693 A | 10/1995 | Conston et al. |
| 5,462,860 A | 10/1995 | Mach |
| 5,478,352 A | 12/1995 | Fowler |
| 5,503,848 A | 4/1996 | Perbellini et al. |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,599,735 A | 2/1997 | Moslehi |
| 5,614,587 A | 3/1997 | Rhee et al. |
| 5,618,551 A | 4/1997 | Tardy et al. |
| 5,643,596 A | 7/1997 | Pruss et al. |
| 5,645,849 A | 7/1997 | Pruss et al. |
| 5,648,506 A | 7/1997 | Desai et al. |
| 5,658,592 A | 8/1997 | Tanihara et al. |
| 5,660,854 A | 8/1997 | Haynes et al. |
| 5,667,839 A | 9/1997 | Berg |
| 5,669,934 A | 9/1997 | Sawyer |
| 5,672,336 A | 9/1997 | Sharma |
| 5,674,275 A | 10/1997 | Tang et al. |
| 5,690,675 A | 11/1997 | Sawyer et al. |
| 5,690,954 A | 11/1997 | Ilium |
| 5,698,213 A | 12/1997 | Jamiolkowski et al. |
| 5,700,476 A | 12/1997 | Rosenthal et al. |
| 5,712,161 A | 1/1998 | Koezuka et al. |
| 5,714,370 A | 2/1998 | Eibl et al. |
| 5,723,308 A | 3/1998 | Mach et al. |
| 5,743,312 A | 4/1998 | Pfeifer et al. |
| 5,749,895 A | 5/1998 | Sawyer et al. |
| 5,752,974 A | 5/1998 | Rhee et al. |
| 5,770,229 A | 6/1998 | Tanihara et al. |
| 5,779,668 A | 7/1998 | Grabenkort |
| 5,791,352 A | 8/1998 | Reich et al. |
| 5,795,330 A | 8/1998 | Tofighi et al. |
| 5,798,091 A | 8/1998 | Trevino et al. |
| 5,804,203 A | 9/1998 | Hang et al. |
| 5,823,671 A | 10/1998 | Mitchell et al. |
| 5,824,015 A | 10/1998 | Sawyer |
| 5,853,749 A | 12/1998 | Hobbs |
| 5,856,356 A | 1/1999 | Tsouderos et al. |
| 5,861,043 A | 1/1999 | Carn |
| 5,863,496 A | 1/1999 | McElhany |
| 5,874,500 A | 2/1999 | Rhee et al. |
| 5,876,372 A | 3/1999 | Grabenkort et al. |
| 5,883,078 A | 3/1999 | Seelich et al. |
| 5,890,610 A | 4/1999 | Jansen et al. |
| 5,895,412 A | 4/1999 | Tucker |
| 5,902,832 A | 5/1999 | Van Bladel et al. |
| 5,908,054 A | 6/1999 | Safabash et al. |

(56) References Cited

U.S. PATENT DOCUMENTS

| | | |
|---|---|---|
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,959,735 A | 9/1999 | Maris et al. |
| 5,986,168 A | 11/1999 | Noishiki et al. |
| 5,997,895 A | 12/1999 | Narotam et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,056,970 A | 5/2000 | Greenawalt et al. |
| 6,063,061 A | 5/2000 | Wallace et al. |
| 6,066,325 A | 5/2000 | Wallace et al. |
| 6,074,663 A | 6/2000 | Delmotte et al. |
| 6,096,309 A | 8/2000 | Prior et al. |
| 6,099,952 A | 8/2000 | Cercone |
| 6,110,484 A | 8/2000 | Sierra |
| 6,113,948 A | 9/2000 | Heath |
| 6,129,761 A | 10/2000 | Hubbell |
| 6,132,759 A | 10/2000 | Schacht et al. |
| 6,162,241 A | 12/2000 | Coury et al. |
| 6,166,130 A | 12/2000 | Rhee et al. |
| 6,168,788 B1 | 1/2001 | Wortham |
| 6,179,872 B1 | 1/2001 | Bell et al. |
| 6,193,670 B1 | 2/2001 | van Tassel et al. |
| 6,218,176 B1 | 4/2001 | Berthold et al. |
| 6,224,862 B1 | 5/2001 | Turecek et al. |
| 6,261,596 B1 | 7/2001 | Li et al. |
| 6,277,394 B1 | 8/2001 | Sierra |
| 6,280,727 B1 | 8/2001 | Prior et al. |
| 6,283,933 B1 | 9/2001 | D'Aiessio et al. |
| 6,300,128 B1 | 10/2001 | Morota et al. |
| 6,303,323 B1 | 10/2001 | Laskey et al. |
| 6,312,474 B1 | 11/2001 | Francis et al. |
| 6,312,725 B1 | 11/2001 | Wallace et al. |
| 6,321,951 B1 | 11/2001 | Frutin |
| 6,328,229 B1 | 12/2001 | Duronio et al. |
| 6,334,865 B1 | 1/2002 | Redmond et al. |
| 6,361,551 B1 | 3/2002 | Torgerson et al. |
| 6,364,519 B1 | 4/2002 | Hughes et al. |
| 6,387,413 B1 | 5/2002 | Miyata et al. |
| 6,391,343 B1 | 5/2002 | Yen |
| 6,416,739 B1 | 7/2002 | Rogerson |
| 6,454,787 B1 | 9/2002 | Maddalo et al. |
| 6,458,380 B1 | 10/2002 | Leaderman |
| 6,458,386 B1 | 10/2002 | Schacht et al. |
| 6,458,889 B1 | 10/2002 | Trollsas |
| 6,461,325 B1 | 10/2002 | Delmotte et al. |
| 6,472,162 B1 | 10/2002 | Coelho |
| 6,495,127 B1 | 12/2002 | Wallace et al. |
| 6,548,081 B2 | 4/2003 | Sadozai et al. |
| 6,584,858 B1 | 7/2003 | Miyazawa et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 6,831,058 B1 | 12/2004 | Ikada et al. |
| 6,861,046 B1 | 3/2005 | Appino et al. |
| 6,887,974 B2 | 5/2005 | Pathak |
| 7,052,713 B2 | 5/2006 | Stimmeder |
| 7,056,722 B1 | 6/2006 | Coelho |
| 7,109,163 B2 | 9/2006 | Pendharkar et al. |
| 7,125,860 B1 | 10/2006 | Renier et al. |
| 7,320,962 B2 | 1/2008 | Reich et al. |
| 7,393,674 B2 | 7/2008 | Jiang et al. |
| 7,427,607 B2 | 9/2008 | Suzuki |
| 7,435,425 B2 | 10/2008 | Qian et al. |
| 7,547,446 B2 | 6/2009 | Qian et al. |
| 7,833,965 B2 | 11/2010 | Pendharkar et al. |
| 7,871,637 B2 | 1/2011 | Qian et al. |
| 7,923,431 B2 | 4/2011 | Wolff |
| 7,927,626 B2 | 4/2011 | Pendharkar et al. |
| 7,935,371 B2 | 5/2011 | Williams |
| 8,071,090 B2 | 12/2011 | Senderoff et al. |
| 8,119,160 B2 | 2/2012 | Looney et al. |
| 8,303,981 B2 | 11/2012 | Wallace et al. |
| 8,357,378 B2 | 1/2013 | Wallace et al. |
| 8,512,729 B2 | 8/2013 | Wallace et al. |
| 8,551,941 B2 | 10/2013 | Pendharkar et al. |
| 8,603,511 B2 | 12/2013 | Wallace et al. |
| 8,642,831 B2 | 2/2014 | Larsen et al. |
| 8,846,105 B2 | 9/2014 | Koopman et al. |
| 9,265,858 B2 | 2/2016 | Larsen |
| 9,376,674 B2 | 6/2016 | Jorquera Nieto et al. |
| 9,533,069 B2 | 1/2017 | Larsen et al. |
| 9,629,798 B2 | 4/2017 | Senderoff et al. |
| 9,724,078 B2 | 8/2017 | Larsen et al. |
| 9,999,703 B2 | 6/2018 | Larsen |
| 10,111,980 B2 | 10/2018 | Larsen |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt et al. |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0027146 A1 | 3/2002 | de LaForcade et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0082620 A1 | 6/2002 | Lee et al. |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0064109 A1 | 4/2003 | Qian et al. |
| 2003/0095993 A1 | 5/2003 | Benz et al. |
| 2003/0162708 A1 | 8/2003 | Wolff |
| 2003/0175410 A1 | 9/2003 | Campbell |
| 2003/0175419 A1 | 9/2003 | Sessa |
| 2003/0181659 A1 | 9/2003 | Naranda et al. |
| 2003/0224056 A1 | 12/2003 | Kotha et al. |
| 2003/0225378 A1 | 12/2003 | Wilkie et al. |
| 2003/0232746 A1 | 12/2003 | Lamberti et al. |
| 2004/0076647 A1 | 4/2004 | Biering |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2004/0267352 A1 | 12/2004 | Davidson et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0186253 A1 | 8/2005 | Lee et al. |
| 2005/0214277 A1 | 9/2005 | Schaufler |
| 2005/0218541 A1 | 10/2005 | Peng et al. |
| 2005/0239675 A1 | 10/2005 | Makansi |
| 2005/0245905 A1 | 11/2005 | Schmidt et al. |
| 2005/0284809 A1 | 12/2005 | Looney et al. |
| 2006/0002890 A1 | 1/2006 | Hersel et al. |
| 2006/0002918 A1 | 1/2006 | Jiang et al. |
| 2006/0052747 A1 | 3/2006 | Nishimura et al. |
| 2006/0067976 A1 | 3/2006 | Ferraro et al. |

(56) References Cited

U.S. PATENT DOCUMENTS

| | | |
|---|---|---|
| 2006/0068013 A1 | 3/2006 | DiTizio et al. |
| 2006/0115805 A1 | 6/2006 | Hansen |
| 2006/0121080 A1 | 6/2006 | Lye et al. |
| 2006/0121104 A1 | 6/2006 | Stern |
| 2006/0147492 A1 | 7/2006 | Hunter et al. |
| 2006/0159733 A1 | 7/2006 | Pendharkar et al. |
| 2006/0167561 A1 | 7/2006 | Odar et al. |
| 2006/0189516 A1 | 8/2006 | Yang et al. |
| 2006/0193846 A1 | 8/2006 | Stimmeder |
| 2006/0204490 A1 | 9/2006 | Pendharkar et al. |
| 2006/0255053 A1 | 11/2006 | Li |
| 2006/0282138 A1 | 12/2006 | Ota |
| 2007/0009578 A1 | 1/2007 | Moller et al. |
| 2007/0025955 A1 | 2/2007 | Lowinger et al. |
| 2007/0086958 A1 | 4/2007 | Drake et al. |
| 2007/0128343 A1 | 6/2007 | Chappa |
| 2007/0160543 A1 | 7/2007 | Moiler |
| 2007/0215235 A1 | 9/2007 | Ranalletta et al. |
| 2007/0250007 A1 | 10/2007 | Shekalim |
| 2007/0264130 A1 | 11/2007 | Mallett |
| 2007/0264301 A1 | 11/2007 | Cleek et al. |
| 2007/0264302 A1 | 11/2007 | Cleek et al. |
| 2008/0085316 A1 | 4/2008 | Qian et al. |
| 2008/0091277 A1 | 4/2008 | Deusch et al. |
| 2008/0095830 A1 | 4/2008 | Van Holten |
| 2008/0109002 A1 | 5/2008 | Delmotte |
| 2008/0199539 A1 | 8/2008 | Baker et al. |
| 2008/0286376 A1 | 11/2008 | Qian et al. |
| 2008/0311172 A1 | 12/2008 | Schapira et al. |
| 2009/0087569 A1 | 4/2009 | Fan et al. |
| 2009/0142396 A1 | 6/2009 | Odar et al. |
| 2009/0157017 A1 | 6/2009 | Ambrosio |
| 2010/0028309 A1 | 2/2010 | Odar et al. |
| 2010/0048758 A1 | 2/2010 | Chen et al. |
| 2010/0063459 A1 | 3/2010 | Preiss-Bloom et al. |
| 2010/0113828 A1 | 5/2010 | Dalsin et al. |
| 2010/0143447 A1 | 6/2010 | Hansen |
| 2010/0256671 A1 | 10/2010 | Falus |
| 2010/0292717 A1 | 11/2010 | Petter-Puchner et al. |
| 2010/0318048 A1 | 12/2010 | Hoeffinghoff et al. |
| 2011/0021964 A1 | 1/2011 | Larsen et al. |
| 2011/0045034 A1 | 2/2011 | Nur et al. |
| 2011/0059228 A1 | 3/2011 | Gillick et al. |
| 2011/0270167 A1 | 11/2011 | Matusch |
| 2012/0121532 A1* | 5/2012 | Goessl .................. A61P 7/04 424/78.35 |
| 2012/0128653 A1 | 5/2012 | Goessl et al. |
| 2012/0201726 A1 | 8/2012 | Pearcy et al. |
| 2013/0108671 A1 | 5/2013 | McCoy et al. |
| 2014/0005636 A1* | 1/2014 | Wang .................. A61M 5/284 604/82 |
| 2014/0220130 A1 | 8/2014 | Larsen et al. |
| 2014/0322791 A1 | 10/2014 | Jorquera Nieto et al. |
| 2015/0037314 A1 | 2/2015 | Larsen |
| 2015/0045830 A1 | 2/2015 | Jensen et al. |
| 2016/0120527 A1 | 5/2016 | Larsen et al. |
| 2016/0354512 A1 | 12/2016 | Larsen |
| 2017/0311939 A1 | 11/2017 | Larsen et al. |
| 2018/0147355 A1 | 5/2018 | Larsen |
| 2018/0243468 A1 | 8/2018 | Larsen |
| 2018/0264194 A1 | 9/2018 | Larsen |
| 2019/0015546 A1 | 1/2019 | Larsen |

FOREIGN PATENT DOCUMENTS

| | | |
|---|---|---|
| CN | 1270240 | 10/2000 |
| DE | 3146841 | 6/1983 |
| DE | 4119140 | 12/1992 |
| DE | 4407875 | 9/1995 |
| EP | 0132983 | 2/1985 |
| EP | 0156649 | 10/1985 |
| EP | 0341007 | 11/1989 |
| EP | 0341745 | 11/1989 |
| EP | 0365705 | 5/1990 |
| EP | 0372966 | 6/1990 |
| EP | 0385916 A2 | 9/1990 |
| EP | 0395758 | 11/1990 |
| EP | 0172710 | 3/1992 |
| EP | 0478827 | 4/1992 |
| EP | 0493387 | 10/1993 |
| EP | 0376931 | 6/1994 |
| EP | 0702081 | 3/1996 |
| EP | 0737467 | 10/1996 |
| EP | 0612252 | 5/1999 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |
| EP | 1084720 | 3/2001 |
| EP | 1140235 | 10/2001 |
| EP | 1174463 | 1/2002 |
| EP | 1258256 | 11/2002 |
| EP | 1283063 | 2/2003 |
| EP | 0790823 | 7/2003 |
| EP | 0891193 | 8/2003 |
| EP | 1484070 | 12/2004 |
| EP | 1 543 842 A1 | 6/2005 |
| EP | 1095064 | 6/2005 |
| EP | 1649867 | 4/2006 |
| EP | 1361906 | 4/2007 |
| EP | 1414370 | 4/2007 |
| EP | 1059957 | 8/2007 |
| EP | 1608230 | 7/2010 |
| EP | 2 040 724 B1 | 10/2011 |
| FR | 2679772 | 5/1993 |
| FR | 2759980 | 8/1998 |
| GB | 648619 | 1/1951 |
| GB | 697603 | 9/1953 |
| GB | 1037937 | 8/1966 |
| GB | 1199887 | 7/1970 |
| GB | 1544080 | 2/1981 |
| GB | 1591654 | 6/1981 |
| GB | 2266239 | 10/1993 |
| GB | 2393120 | 3/2004 |
| GB | 2414021 | 11/2005 |
| JP | 51-125156 | 11/1976 |
| JP | 59-113889 | 6/1984 |
| JP | 60214728 | 10/1985 |
| JP | 62070318 | 3/1987 |
| JP | 62221357 | 9/1987 |
| JP | 0282316 | 9/1988 |
| JP | 01130519 | 5/1989 |
| JP | 05308969 | 11/1993 |
| JP | 06254148 | 9/1994 |
| JP | H07090241 | 4/1995 |
| JP | 08-024325 | 1/1996 |
| JP | 9-504719 | 5/1997 |
| JP | 10-507666 | 7/1998 |
| JP | 2002/513308 | 5/2002 |
| JP | 2004002271 | 1/2004 |
| JP | 2004147959 | 5/2004 |
| JP | 2006-296896 | 11/2006 |
| JP | 2010228932 | 10/2010 |
| JP | 2011212182 A | 10/2011 |
| KR | 910007847 | 10/1991 |
| KR | 100751046 | 8/2007 |
| WO | WO 83/01244 | 4/1983 |
| WO | wo 86/00912 | 2/1986 |
| WO | WO 89/02730 | 4/1989 |
| WO | WO 90/13320 | 11/1990 |
| WO | WO 92/21354 | 12/1992 |
| WO | WO 92/22252 | 12/1992 |
| WO | WO 93/06802 | 4/1993 |
| WO | WO 93/06855 | 4/1993 |
| WO | WO 93/10768 | 6/1993 |
| WO | WO 93/21908 | 11/1993 |
| WO | WO 94/08552 | 4/1994 |
| WO | WO 94/17840 | 8/1994 |
| WO | WO 94/27630 | 12/1994 |
| WO | WO 95/12371 | 5/1995 |
| WO | WO 95/15747 | 6/1995 |
| WO | WO 95/25748 | 9/1995 |

(56) References Cited

FOREIGN PATENT DOCUMENTS

| | | |
|---|---|---|
| WO | WO 95/31955 | 11/1995 |
| WO | WO 96/04025 | 2/1996 |
| WO | WO 96/06883 | 3/1996 |
| WO | WO 96/07472 | 3/1996 |
| WO | WO 96/10374 | 4/1996 |
| WO | WO 96/10428 | 4/1996 |
| WO | WO 96/12447 | 5/1996 |
| WO | WO 96/14368 | 5/1996 |
| WO | WO 96/16643 | 6/1996 |
| WO | WO 96/39159 | 12/1996 |
| WO | WO 96/40033 | 12/1996 |
| WO | WO 97/17023 | 5/1997 |
| WO | WO 97/17024 | 5/1997 |
| WO | WO 97/17025 | 5/1997 |
| WO | WO 97/29792 | 8/1997 |
| WO | WO 97/37694 | 10/1997 |
| WO | WO 98/08550 | 3/1998 |
| WO | WO 98/31403 | 7/1998 |
| WO | WO 98/34546 | 8/1998 |
| WO | WO 98/36784 | 8/1998 |
| WO | WO 98/43092 | 10/1998 |
| WO | WO 98/44963 | 10/1998 |
| WO | WO 98/51282 | 11/1998 |
| WO | WO 99/04828 | 2/1999 |
| WO | WO 99/12032 | 3/1999 |
| WO | WO 99/13902 | 3/1999 |
| WO | WO 99/38606 | 8/1999 |
| WO | WO 99/44901 | 9/1999 |
| WO | WO 99/45938 | 9/1999 |
| WO | WO 99/051208 | 10/1999 |
| WO | WO 00/09018 | 2/2000 |
| WO | WO 00/18301 | 4/2000 |
| WO | WO 00/27327 | 5/2000 |
| WO | WO 00/61201 | 10/2000 |
| WO | WO 00/74742 | 12/2000 |
| WO | WO 00/76533 | 12/2000 |
| WO | WO 01/13956 | 3/2001 |
| WO | WO 01/28603 | 4/2001 |
| WO | WO 01/34206 | 5/2001 |
| WO | WO 01/54735 | 8/2001 |
| WO | WO 01/66161 | 9/2001 |
| WO | WO 01/97826 | 12/2001 |
| WO | WO 01/97871 A2 | 12/2001 |
| WO | WO 02/18450 | 3/2002 |
| WO | WO 02/22059 | 3/2002 |
| WO | WO 02/22184 | 3/2002 |
| WO | WO 02/40068 | 5/2002 |
| WO | WO 02/058749 | 8/2002 |
| WO | WO 02/064182 | 8/2002 |
| WO | WO 02/070594 | 9/2002 |
| WO | WO 02/072128 A1 | 9/2002 |
| WO | WO 03/007845 | 1/2003 |
| WO | WO 2003/004072 | 1/2003 |
| WO | WO 03/024426 | 3/2003 |
| WO | WO 03/024429 | 3/2003 |
| WO | WO 03/055531 | 7/2003 |
| WO | WO 2003/070110 | 8/2003 |
| WO | WO 03/094983 | 11/2003 |
| WO | WO 04/028404 | 4/2004 |
| WO | WO 04/028423 | 4/2004 |
| WO | WO 04/029095 | 4/2004 |
| WO | WO 04/030711 | 4/2004 |
| WO | WO 2004/028583 | 4/2004 |
| WO | WO 2004/035629 | 4/2004 |
| WO | WO 2004/053051 | 6/2004 |
| WO | WO 04/075650 | 9/2004 |
| WO | WO 04/084869 | 10/2004 |
| WO | WO 04/108035 | 12/2004 |
| WO | WO 2004/108179 | 12/2004 |
| WO | WO 2004/108418 A1 | 12/2004 |
| WO | WO 05/000265 | 1/2005 |
| WO | WO 2005/002510 A2 | 1/2005 |
| WO | WO 05/009225 | 2/2005 |
| WO | WO 05/041811 | 5/2005 |
| WO | WO 05/044285 | 5/2005 |
| WO | WO 05/062889 | 7/2005 |
| WO | WO 05/063217 A1 | 7/2005 |
| WO | WO 2005/072700 | 8/2005 |
| WO | WO 2005/084650 A1 | 9/2005 |
| WO | WO 05/107713 | 11/2005 |
| WO | WO 2006/005340 | 1/2006 |
| WO | WO 2006/009989 A1 | 1/2006 |
| WO | WO 2006/031358 | 3/2006 |
| WO | WO 06/034568 | 4/2006 |
| WO | WO 06/063758 | 6/2006 |
| WO | WO 2006/058435 A2 | 6/2006 |
| WO | WO 06/128471 | 12/2006 |
| WO | WO 2007/001926 | 1/2007 |
| WO | WO 2007/018887 A2 | 2/2007 |
| WO | WO 2007/092618 A2 | 8/2007 |
| WO | WO 2007/133699 | 11/2007 |
| WO | WO 2007/137839 | 12/2007 |
| WO | WO 2008/016983 | 2/2008 |
| WO | WO 2008/019127 A2 | 2/2008 |
| WO | WO 2008/051758 | 5/2008 |
| WO | WO 2008/060475 A2 | 5/2008 |
| WO | WO 2008/090555 | 7/2008 |
| WO | WO 2008/157304 A2 | 12/2008 |
| WO | WO 2009/109194 | 9/2009 |
| WO | WO 2009/109963 | 9/2009 |
| WO | WO 2009/123903 | 10/2009 |
| WO | WO 2009/131752 A2 | 10/2009 |
| WO | WO 2011/047753 A1 | 4/2011 |
| WO | WO 2011/083154 A1 | 7/2011 |
| WO | WO 2011/151384 | 12/2011 |
| WO | WO 2011/151386 | 12/2011 |
| WO | WO 2011/151400 | 12/2011 |
| WO | WO 2012/146655 | 11/2012 |
| WO | WO 2013/053753 | 4/2013 |
| WO | WO 2013/053755 | 4/2013 |
| WO | WO 2013/053759 | 4/2013 |
| WO | WO 2013/060770 | 5/2013 |
| WO | WO 2013/131520 A2 | 9/2013 |
| WO | WO 2013/185776 A1 | 12/2013 |
| WO | WO 2014/086996 | 6/2014 |
| WO | WO 2014/0202760 A2 | 12/2014 |
| WO | WO 2015/086028 A1 | 6/2015 |
| WO | WO 2016/058612 A1 | 4/2016 |
| WO | WO 2017/005590 | 1/2017 |
| WO | WO 2017/098493 A1 | 6/2017 |

OTHER PUBLICATIONS

"Gelfoam Prescribing Information," Pharmacia & Upjohn (Nov. 1996).
"Gelfoam® Product Brochure," Pharmacia & Upjohn (Jun. 2013).
26th Annual Symposium: Clinical Update In Anaesthesiology, Surgery and Perioperative Medicine, Jan. 20-25, 2008.
Ansell, J., et al., "Gelfoam and Autologous Clot Embolization: Effect on Coagulation," *Investigative Radiology*, 13: 115-120 (1978).
Arai, K., et al., "Clinical Effect of Thrombin-Collagen Sponge Sheet in Surgical Field," Chiryo (Pharmacology and Treatment), 11(5):413-418 (1983). (English translation of Office Action for Japanese counterpart application 2010-547957, Title: Device for Promotion of Hemostasis and/or Wound Healing, being provided to satisfy "concise explanation" requirement under 37 C.F.R. 1.98(a)(3)).
Barrow, D.L., et al., "The Use of Greater Omentum Vascularized Free Flaps for Neurosurgical Disorders Requiring Reconstruction", *Journal of Neurosurgery*, 60: 305-311 (1984).
Barton, B., et al., "Fibrin Glue as a Biologic Vascular Patch—A Comparative Study," *Journal of Surgical Research*, vol. 40, 1 page; abstract retrieved from http://www.ncbi.nlm.nih.gov on Jan. 3, 2001. (1986).
Baxter, "GentaFleece Collagen Fleece—Version 5: Instructions for Use—Collagen Sponge with Antibiotic Protection for Surgical Use," Retrieved from http://www.advancingbiosurgery.com/en_EU/downloads/ifu_gentafleece.pdf on Mar. 2002, 2 pages. English portion second column of first page.
Baxter, "Product Catalogue: Collagen," 4 pages, retrieved from http://www.baxter-ecommerce.com/ecatalog on Feb. 2, 2006 (2006).

(56) References Cited

OTHER PUBLICATIONS

Baxter, "TissuFleece E Package Leaflet," *Baxter International Inc.*, 4 pages, English portion of instructions for use (2003).

Baxter, "TissuFleece E, TissuCone E and TissuFoil E: Biomaterials," *Basic scientific Information*, 9 pages (2003).

Boland, T., et al., "Application of Inkjet Printing to Tissue Engineering," *Biotechnol. J.*, 1: 910-917 (2006).

Boyers, S., et al., "Reduction of Postoperative Pelvic Adhesions in the Rabbit with Gore-Tex Surgical Membrane", *Fertility and Sterility*, 49(6,): 1066-1070 (1988).

Brannon-Peppas, L., et al., "The Equilibrium Swelling Behavior of Porous and Non-Porous Hydrogels," *Absorbent Polymer Technology, Elsevier*, Amsterdam, pp. 67-102 (1990).

Branski, R.C., et al., "Mucosal Wound Healing in a Rabbit Model of Subglottic Stenosis"; *Arch Otolaryngol Head Neck Surg*, vol. 131, Feb. 2005, p. 153-157.

Brunt and Klausner, "Growth factors speed wound healing", *Nature Biotechnology*, 6(1): 25-30 (1988).

Campbell, P.G., et al., "Engineered Spatial Patterns of FGF-2 Immobilized on Fibrin Direct Cell Organization," *Biomaterials*, 26: 6762-6770 (2005).

Campbell, P.G., et al., "Tissue Engineering with the Aid of Inkjet Printers," *Expert Opin. Biol. Ther.*, 7: 1123-1127 (2007).

Canal, T., et al., "Correlation Between Mesh Size and Equilibrium Degree of Swelling of Polymeric Networks" *Biomedical Materials Research*, 23: 1183-1193 (1989).

Cantor, M.O., et al., "Gelfoam® and Thrombin in treatment of massive gastroduodenal hemorrhage—A preliminary report", *American Journal of Surgery*, 883-887 (Dec. 1950).

Cantor, M.O., et al., "Gelfoam and Thrombin in Gastroduodenal Bleeding: An Experimental Study," *Journal of Laboratory and Clinical Medicine*, 35(6): 890-893 (1950).

Cantor, M.O., et al., "Gelfoam and Thrombin in Treatment of Massive Upper Gastrointestinal Hemorrhage," *American Journal of Surgery*, 82(2): 230-235 (Aug. 1951).

Cascone, M.G., et al., "Collagen and hyaluronic acid based polymeric blends as drug delivery systems for the release of physiological concentrations of growth hormone." *Journal of Materials science : Materials in Medicine*, 5: 770-774 (1994).

Changez, M., et al., Abstract of "Efficacy of antibiotics-loaded interpenetrating network (IPNs) hydrogel based on poly (acrylic acid) and gelatin for treatment of experimental osteomyelitis: in vivo study.", *Biomaterials*; 26(14): 2095-2104 (2005).

Chaplin, J.M., et al., "Use of an Acellular Dermal Allograft for Dural Replacement: An Experimental Study," *Neurosurgery*, 45(2): 320-327 (1999).

Cheung, D., et al., "Mechanism of Crosslinking of Proteins by Glutaraldehyde IV: In Vitro and In Vivo Stability of a Crosslinked Collagen Matrix," *Connective Tissue Research*, 25: 27-34 (1990).

Choi, Y.S., et al., "Studies on Gelatin-Based Sponges. Part III: A Comparative Study of Cross-linked Gelatin/ Alginate, Gelatin/ Hyaluronate and Chitosan/Hyaluronate Sponges and their Application as a wound dressing in fullthickness skin defect of rat.", *J. Of Mat. Sci.; Mat. In Med.*; 12: 67-73 (Jan. 2001).

Choi, Y.S., et al., "Studies on gelatin-containing artificial skin: II. Preparation and characterization of cross-linked gelatin-hyaluronate sponge.", *J. Biomed Mater Res.*, 48: 631-639 (1999).

Christensen, F, et al., "Qualitative Description of the Wurster-Based Fluid-Bed Coating Process," *Drug Dev and Industry Pharmacy*, 23(5): 451-463 (1977).

Chronic Wound Care Guidelines © 2007 http://woundheal.org. documents/final_pocket guide_treatment.aspx.

Chuang, V.P., et al., "Sheath Needle for Liver Biopsy in High-Risk Patients" *Radiology*, 166: 261-262 (1988).

Coenye, K.E., et al., "A Qualitative Morphological comparison of Two Heamostatic Agents in a Porcine Liver Trauma Model," *Surgical Science*, 4: 359-364 (2013).

Collins, D., et al., "Enemata of Gelfoam Milk Suspension Combined with Thrombin-Solution to Control Massive Hemorrhage Following Anorectal Surgery," *The American Journal of Proctology*, 2: 60-63 (1951).

Collins, R., et al., "Use of Collagen Film as a Dural Substitute: Preliminary Animal Studies," *Journal of Biomedical Materials Research*, 25: 267-276 (1991).

De la Torre, R.A., et al., "Hemostasis and Hemostatic agents in minimally invasive surgery", *Surgery*, 142(4S): S39-S45 (2007).

De laco, P.A., et al., "Efficacy of a Hyaluronan Derivative gel in postsurgical adhesion prevention in the presence of inadequate hemostasis." *Surgery*, 130(1): 60-64 (2001).

DeLustro, F., et al., "A Comparative Study of the Biologic and Immunologic Response To Medical Devices Derived From Dermal Collagen," *Journal of Biomedical Materials Research*, 20: 109-120 (1986).

Dembo, M.A., et al., Abstract of "Antiseptic hemostatic preparations, their properties and study", Lech. Prep. Krovi Tkanei; pp. 139-140 (1974).

Dodd, G.D., et al., "Minimally invasive treatment of malignant hepatic tumors. At the threshold of a major breakthrough", *Radiographies*, 20: 9-27 (2000).

Drognitz, O., et al., Abstract of "Release of vancomycin and teicoplanin from a plasticized and resorbable gelatin sponge: in vitro investigation of a new antibiotic delivery system with glycopeptides"; *Indection Germany* (Minich); 34(1): 29-34 (2006).

Duchene, D., et al., "Pharmaceutical and Medical Aspects of Bioadhesive Systems for Drug Administration," *Drug Dev and Industr Pharmacy*, 14(2&3):283-318 (1988).

Edgerton, M., et al., "Vascular Hamatomas and Hemagiomas: Classification and Treatment," *Southern Medical Journal*, 75(12): 1541-1547 (1982).

Ellegala, D.B., et al., "Use of FloSeal Hemostatic Sealant in Transsphenoidal Pituitary Surgery: Technical Note."; *Neurosurgery*, 51: 513-516 (Aug. 2002).

English Derwent Abstract of Ranjane reference, Nov. 18, 1997.

Filippi, R., et al., "Bovine Pericardium for Duraplasty: Clinical Results in 32 Patients," *Neurological Review*, 20:103-107 (2001).

Fiss, I., et al., "Use of Gelatin-Thrombin Hemostatic Sealant in Cranial Neurosurgery," *Neurologia Medico-Chirurgica*, 47(10):462-467 (2007).

Flory, P., "Phase Equilibria in Polymer Systems," *Principles of Polymer Chemistry*, 13: 541-594 (1953).

FloSeal Matrix Hemostatic Sealant, Instructions for Use, Retrieved from Internet URL http://www.ctsnet.org/file/vendors/931/pdf/140. pdf [retrieved on Aug. 17, 2005].

Fujii, Y., et al., "Safety of GT XIII (Report 2)—Japanese + English translation," *The Clinical Report*, 20(17) (Dec. 1986).

Gall, R.M., "Control of Bleeding in Endoscopic Sinus Surgery: Use of a Novel Gelatin-Based Hemostatic Agent", *Journal of Otolaryngology*, 31(5): (2002).

Gibble, J.W., et al., "Fibrin glue: the perfect operative sealant?" *Reviews: Transfusion*, 30(8): 741-747 (1990).

Guinto, F., "Preparation of Gelfoam Particles Using an Orthopedic Rasp," *Radiology*, 153: 250 (1984).

Gurny, R., et al., "Bioadhesive Intraoral Release Systems: Design, Testing and Analysis," *Biomaterials*, 5: 336-340 (1984).

Hae-Won, K., et al., Abstract of "Porus scaffolds of gelatin-hydroxyapatite nanocomposites obtained by biometic approach: Characterization and antibiotic drug release."; *J. of Biomedical Materials Research*, 74B(2): 686-698 (2005).

Harris, W.H., et al., "Topical Hemostatic Agents for Bone Bleeding in Humans," *The Journal of Bone and Joint Surgery*, 60-A(4): 454-456 (1978).

Heller, J., et al., "Release of Norethindrone from Poly(Ortho Esters)," *Polymer Engineering and Science*, 21: 727-731 (1981).

Herndon, J., et al., "Compression of the Brain and Spinal Cord Following Use of Gelfoam," *Arch. Surg*, 104: 107 (Jan. 1972).

Hieb, L., et al., "Spontaneous Postoperative Cerebrospinal Fluid Leaks Following Application of Anti-Adhesion Barrier Gel," *Spine*, 26(7): 748-751 (2001).

(56) References Cited

OTHER PUBLICATIONS

Hill, et al., "Use of microfibrillar collagen hemostat (avitenet) and thrombin to achieve hemostats after median sternotomy."; *J. Thorac Cardiovasc Surg.*, 108: 1151-1152 (1994).

Hill-West, J.L., et al., "Efficacy of a resorbable hydrogel barrier, oxidized regenerated cellulose and hyaluronic acid in the prevention of ovarian adhesions in a rabbit model."; *Fertility and Sterility*, 62(3): 630-634 (1994).

Hong, S.R., et al., Abstract of "Study on gelatin-containing artificial skin IV: a comparative study on the effect of antibiotic and EGF on cell proliferation during epidermal healing."; *Biomaterials*, 22(20): 2777-2783 (2001).

Hong, Y.M., et al., "The Use of Hemostatic Agents and Sealants in Urology", *The Journal of Urology*, 176: 2367-2374 (2006).

Hood, D., et al., "Efficacy of Topical Hemostat Floseal Matrix in Vascular Surgery," *24th World Congress of the International Society for Cardiovascular Surgery*, Sep. 12-16, 1999, 2 pages.

Hotz, G., et al., "Collagen and Fibrin as Biologic Binders from Granular Hydroxyapatite," *Deutsche Zeitschrift fur Mund-Kieferund Gesichts-Chirurgie*, 13(4): 296-300 (1989). Abstract retrieved from http://www.ncbi.nlm.nih.gov on Jan. 3, 2001.

Hutchinson, R. W., et al., "An In Vivo Comparison of Hemostatic Gelatin Matrix Products in a Porcine Spleen Biopsy-punch Model", Surgical Technology International XXVII, 2015.

Jeong, B., et al., "Biodegradable Block Copolymers as Injectable Drug-Delivery Systems," *Nature*, 388: 860-862 (1997).

Jonas, R., et al., "A new sealant for knitted Dacron prostheses: Minimally cross-linked gelatin," *Journal of Vascular Surgery*, 7(3): 414-419 (1988).

Katayama, T., et al., "GT XIII safety ($3^{rd}$ report)—Japanese + English translation," *The Clinical Report*, vol. 20 (1986).

Kelly M.J. et al., "The value of an operative wound swab sent in transport medium in the prediction of later clinical wound infection: A controlled clinical and bacteriological evaluation.", *Brit. J. Surgery*, 65: 81-88 (1978).

Kim, K., et al., "Reduction in Leg Pain and Lower-Extremity Weakness with Oxiplex/SP Gel for 1 Year after Laminevtomy, Laminotomy, and Disectomy," *Neurosurgical Focus*, 17: 1-6 (2004).

Kline, D., et al., "Dural Replacement with Resorbable Collagen," *Archives of Surgery*, 91: 924-929 (1965).

Knopp, U., "A New Collagen Foil Versus a Cadaveric Dura Graft for Dural Defects—A Comparative Animal Experimental Study," *European Association of Neurosurgical Societies—Proceedings of the $12^{th}$ European Congress of Neurosurgery*, Lisbon, 17 pages (2003).

Koçak, I., et al., "Reduction of adhesion formation with cross-linked hyaluronic acid after peritoneal surgery in rats.", *Fertility and Sterility*, 72(5): 873-878 (1999).

Kofidis, T., et al., "Clinically Established Hemostatis Scaffold (Tissue Fleece) as Biomatrix in Tissue and Organ Engineering Research," *Tissue Engineering*, 9: 517-523 (2003).

Kost J., and Langer R., "Equilibrium Swollen Hydrogels in Controlled Release Applications," *Ch. 5: Hydrogels in Medicine and Pharmacy, vol. III: properties and Applications*, N. Peppas ed., pp. 95-108 (1987).

Krill, D., et al., "Topical Thrombin and Powdered Gelfoam: An Efficient Hemostatic Treatment for Surgery," *Journal of Tennessee Dental Association*, 66(2): 26-27 (1986).

Kuhn, J., et al., "Bilateral Subdural Heamatomata and Lumbar Pseudomeningocele Due to a Chronic Leakage of Liquor Cerebrospinalis after a Lumbar Disectomy with the Application of ADCON-L Gel," *Journal of Neurology, Neurosergery & Psychiatry*, 76: 1031-1033 (2005).

Langer, R., et al., "Chemical and Physical Structure of Polymers as Carriers for Controlled Release of Bioactive Agents: A Review," *Journal of Macromolecular Science—Reviews in Macromolecular Chemistry and Physics*, C23: 61-126 (1983).

Laquerriere, A., et al., "Experimental Evaluation of Bilayered Human Collagen as a Dural Substitute," *Journal of Neurosurgery*, 78: 487-491 (1993).

Larson, P., "Topical Hemostatic Agents for Dermatologic Surgery," *Journal of Dermatologic Surgery & Oncology*, 14: 623-632 (1988).

Larsson, B., et al., "Surgicel®—an absorbable hemostatic material-in prevention of peritoneal adhesion in rats."; *Acta Chir Scand.*, 26(144): 375-378 (1978).

Laurent, C., et al., "Hyaluronic acid reduces connective tissue formation in middle ears filled with absorbable gelatin sponge: An experimental study.", *AM. J.Otolaryngol*, 7: 181-186 (1986).

Le, A., et al., "Unrecognized Durotomy After Lumbar Discectomy: A Report of Four Cases Associated with the Use of ADCON-L," *Spine*, 26(1): 115-118 (2001).

Lee, J., et al., "Experimental Evaluation of Silicone-Coated Dacron and Collagen Fabric-Film Laminate as Dural Substitutes," *Journal of Neurosurgery*, 27: 558-564 (1967).

Lee, P., "Interpretation of Drug-Release Kinetics from Hydrogel Matrices in Terms of Time-Dependent Diffusion Coefficients," Controlled-Release Technology—Pharmaceutical Applications, Ch. 5, *ACS Symposium Series 348*, pp. 71-83 (1986).

Leong, K., et al., "Polyanhydrides for Controlled Release of Bioactive Agents," *Biomaterials*, 7: 364-371 (1986).

Leong, K., et al., "Polymeric Controlled Drug Delivery," *Advanced Drug Delivery Reviews*, 1: 199-233 (1987).

Lewis, K., et al., "Comparison of Two Gelatin and Thrombin Combination Hemostats in a Porcine Liver Abrasion Model," *Journal of Investigative Surgery*, 26: 141-148 (2013).

Li, G., et al., "Evaluation of esterified hyaluronic acid as middle ear-packing material.", *Arch Otolaryngol Head Neck Surg*, 127: 534-539 (2001).

Loeb, J, "The Influence of Electrolytes Upon the Osmotic Pressure of Gelatin Solutions", *J. Biol. Chem.*, 35: 497-508 (1918).

Luengo, J., et al., "Prevention of peritoneal adhesions by the combined use of Spongostan and 32% Dextran 70: An experimental study in pigs." *Fertility and Sterility*, 29(4): 447-450 (1978).

Masar, E., et al., "Synthesis of Polyurethanes and Investigation of their Hydrolytic Stability," *Journal of Polymer Science: Polymer Symposium*, 66: 259-268 (1979).

Masuzawa, M., et al., "Experimental Study Related to the Hemostasis Action of GT XIII," *The Clinical Report*, 20(2): 471-476 (Feb. 1986).

Matsumoto, K., et al., "A Gelatin Coated Collagen—Polyglycolic Acid Composite Membrane as a Dural Substitute," *American Society for Artificial Internal Organs Journal*, 47: 641-645 (2001).

Maurer, P, et al., "Vicryl (Polyglactin 910) Mesh as a Dural Substitute," *Journal of Neurosurgery*, 63:448-452 (1985).

Maxson, W.S., et al., "Efficacy of a modified oxidized cellulose fabric in the prevention of adhesion formation." *Gynecol. Obstet. Invest.*, 26: 160-165 (1988).

McClure, J., et al., "Massive Gastroduodenal Hemorrhage: Treatment with Powdered Gelfoam and Buffered Thrombin Solution," *Surgery*, 32: 630-637 (1952).

McPherson, J., et al., "An Examination of the Biologic Response to Injectable, Glutaraldehyde Cross-linked Collagen Implants," *Journal of Biomedical Materials Research*, 20: 93-107 (1986).

McPherson, J., et al., "Development and Biochemical Characterization of Injectable Collagen," *J. Dermatol. Surg. Oncol.*, 12(1): 13-20 (Jul. 7, 1988).

McPherson, J., et al., "The Effects of Heparin on the Physiochemical Properties of Reconstituted Collagen," *Collagen and Related Research*, 1: 65-82 (1988).

McPherson, J., et al., "The Preparation and Physiochemical Characterization of an Injectable Form of Reconstituted, Glutaraldehyde Crosslinked, Bovine Corium Collagen," *Journal of Biomedical Materials Research*, 20: 79-92 (1986).

Meddings, N., et al., "Collagen Vicryl-A New Dural Prosthesis," *Acta Neurochirurgica*, 117: 53-58 (1992).

Mello, L., et al., "Duraplasty with Biosynthetic Cellulose: An Experimental Study," *Journal of Neurosurgery*, 86: 143-150 (1997).

Miller, D., and Peppas, N., "Diffusional Effects During Albumin Adsorption on Highly Swollen Poly(vinyl Alcohol) Hydrogels," *Eur. Polym. J.*, 24(7): 611-615 (1988).

Miller, E.D., et al., "Dose-Dependent Cell Growth in Response to Concentration Modulated Patterns of FGF-2 Printed on Fibrin," *Biomaterials*, 27: 2213-2221 (2006).

(56) References Cited

OTHER PUBLICATIONS

Millikan, L., "Treatment of Depressed Cutaneous Scars with Gelatin Matrix Implant: A Multicenter Study," *J. Am. Acad. Dermatol.*, 16: 1155-1162 (1987).
Min et al., "Molecular Weight Changes of Sodium Hyaluronate Powder and Solution by Heat treatment," Matrix Biology Institute, Proceedings of Hyaluronan, Oct. 11-16, 2003.
Mitsuhashi, J., "Invertabrate Tissue Culture Methods," *Springer Lab Manual*, p. 407 (2002).
Moak, E., "Hemostatic Agents: Adjuncts to Control Bleeding," *Today's O.R. Nurse*, pp. 6-10 (1991).
Mueller, K., "Release and Delayed Release of Water-Soluble Drugs from Polymer Beads with Low Water Swelling," *Controlled-Release Technology—Pharmaceutical Applications*, Ch. 11, ACS Symposium Series, 348: 139-157 (1986).
Muranyi, et al., "Development of gel-forming lyophilized formulation with recombinant human thrombin", *Drug Development and Industrial Pharmacy* 41(9): (2015) 1566-1573. (Abstract Only).
Narotam, P., et al., "A Clinicopathological Study of Collagen Sponge as a Dural Graft in Neurosurgery," *Journal of Neurosurgery*, 82: 406-412 (1995).
Narotam, P., et al., "Experimental Evaluation of Collagen Sponge as a Dural Graft," *British Journal of Neurosurgery*, 7: 635-641 (1993).
Nimni, M., et al., "Chemically Modified Collagen: A Natural Biomaterial for Tissue Replacement," *Journal of Biomedical Materials Research*, 21: 741-771 (1987).
Nimni, M., Ph.D., "The Cross-Linking and Structure Modification of the Collagen Matrix in the Design of Cardiovascular Prosthesis," *Journal of Cardiac Surgery*, 3: 523-533 (1988).
Nogueira, L., et al., Comparison of gelatine matrix-thrombin sealants used during laparoscopic partial nephrectomy, *BJU International*, 102: 1670-1674 (2008).
Novak, D., "Embolization Materials," *Interventional Radiology*, pp. 295-313 (1990).
O'Neill, P., et al., "Use of Porcine Dermis as a Dural Substitute in 72 Patients," *Journal of Neurosurgery*, 61: 351-354 (1984).
Ofner, C.M. and Bubnis, W.A., "Chemical and Swelling Evaluations of Amino Group Crosslinking in Gelatin and Modified Gelatin Matrices," *Pharma. Res.*, 13: 1821-1827 (1996).
Oyelese, Yinka, et al., "Postpartum Hemhorrage," *Obstetrics and Gynecology Clinics of North America* 34.3, 421-441 (2007).
Oz, M.C., et al., "Controlled clinical trial of a novel hemostatic agent in cardiac surgery.", *Ann Thorac Surg*, 69: 1376-1382 (2000).
Oz, M.C., et al., "Floseal-Matrix: New Generation Topical Hemostatic Sealant", *J. Card. Surg.*, 18: 486-493 (2003).
Palm, S., et al., "Dural Closure with Nonpenetrating Clips Prevents Meningoneural Adhesions: An Experimental Study in Dogs," *Neurosurgery*, 45(4): 875-882 (1999).
Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochirurgica*, 139: 827-838 (1997).
Park, Y-K., et al., "Prevention of Arachnoiditis and Postoperative Tethering of the Spinal Cord with Gore-Tex Surgical Membrane: An Experimental Study with Rats," *Neurosurgery*, 42(4): 813-824 (1998).
Peppas, N. and Barr-Howell, B., "Characterization of the Cross-Linked Structure of Hydrogels," Ch. 2: Hydrogels in Medicine and Pharmacy, vol. I: *Fundamentals*, N. Peppas ed., pp. 27-56 (1986).
Peppas, N. and Brannon-Peppas, L, "Hydrogels at Critical Conditions. Part 1. Thermodynamics and Swelling Behavior," *Journal of Membrane Science*, 48: 281-290 (1990).
Peppas, N. and Khare, A., "Preparation, Structure and diffusional Behavior of Hydrogels in Controlled Release," *Adv. Drug Delivery Reviews*, 11: 1-35 (1993).
Peppas, N. and Korsmeyer, R, "Dynamically Swelling Hydrogels in Controlled Release Applications," Ch. 6: Hydrogels in Medicine and Pharmacy, vol. III: *Properties and Applications*, N. Peppas ed., pp. 109-135 (1987).

Peppas, N. and Lustig, S., "Solute Diffusion in Hydrophilic Network Structures," Ch. 3: Hydrogels in Medicine and Pharmacy, vol. I: *Fundamentals*, N. Peppas ed., pp. 57-83 (1986).
Peppas, N. and Mikos, A., "Preparation Methods and Structure of Hydrogels," Ch. 1: Hydrogels in Medicine and Pharmacy, vol. I: *Fundamentals*, N. Peppas ed., pp. 1-25 (1986).
Peppas, N. and Moynihan, H, "Structure and Physical Properties of Poly(2- Hydroxyethyl Methacrylate) Hydrogels," Ch. 2: Hydrogels in Medicine and Pharmacy, vol. II: *Polymers*, N. Peppas ed., pp. 49-64 (1987).
Peppas, N., "Hydrogels and Drug Delivery," *Current Opinion in Colloid & Interface Science*, 2: 531-537 (1997).
Peppas, N., "Hydrogels in Medicine and Pharmacy," *Hydrogels in Medicine and Pharmacy*, vol. 1. Fundamentals, CRC Press, Boca Raton, FL, 180 pages (1986).
Peppas, N., "Hydrogels in Medicine and Pharmacy," *Hydrogels in Medicine and Pharmacy*, vol. 2. Polymers, CRC Press, Boca Raton, FL, 172 pages (1987).
Peppas, N., "Hydrogels in Medicine and Pharmacy," *Hydrogels in Medicine and Pharmacy*, vol. 3. Properties and Applications, CRC Press, Boca Raton, FL, 196 pages (1987).
Peppas, N., "Hydrogels of Poly (Vinyl Alcohol) and its Copolymers," Ch. 1: Hydrogels in Medicine and Pharmacy, vol. II: *Polymers*, N. Peppas ed., p. 57 p. (1987).
Peppas, N., ed., "Other Biomedical Applications of Hydrogels," Ch. 9: Hydrogels in Medicine and Pharmacy, vol. III: *Properties and Applications*, pp. 177-186 (1987).
Pietrucha, K., "New Collagen Implant as Dural Substitute," *Biomaterials*, 12: 320-323 (1991).
Pitt, C., et al., "Biodegradable Drug Delivery Systems Based on Aliphatic Polyesters: Application to Contraceptives and Narcotic Antagonists," *Controlled Release of Bioactive Materials*, R. Baker, ed., (NY: Academic Press) pp. 19-43 (1980).
Porchet, F., et al., "Inhibition of Epidural Fibrosis with ADCON-L: Effect on Clinical Outcome One Year Following Reoperation for Recurrent Lumbar Radiculopathy," *Neurological Research*, 21: 551-560 (1999).
Product leaflet for FloSeal ®Matrix Hemostatic Sealant dated Jul. 2001 (Jul. 2001).
Pschyrembel®—Klinisches Wörterbuch, 261st edition, de Gruyter (2007).
Purdy, P.D., et al., "Microfibrillar collagen model of canine cerebral infarction"; *Strokes*, 20(10): 1361-1367 (Oct. 1989).
Quintavalla, J., et al., "Fluorescently labeled mesenchymal stem cells (MSCs) maintain mutlilineage potential and can be detected following implantation into Particular cartilage defects.", *Biomaterials*, 23: 109-119 (2002).
Raftery, A., "Absorbable haemostatic materials and intraperitoneal adhesion formation."; Br. J. Surg. 67; 1980; pp. 57-58.
Ratner, B., "Hydrogel Surfaces," Ch. 4: Hydrogels in Medicine and Pharmacy, vol. I: *Fundamentals*, N. Peppas ed., pp. 85-94 (1986).
Raul, J.S., et al., "Utilisation du Polyester Urethane (Neuropatch) Comme Substitut Dural," *Neurochirugie*, 49: 83-89, English abstract only on p. 83 (2003).
Reddy, M., et al., "A Clinical Study of a Fibrinogen-Based Collagen Fleece for Dural repair in Neurosergery," *Acta Neurochirurgica*, 144: 265-269 (2002).
Reese, A.C., "Role of fibronectin in wound healing", Report date: Sep. 12, 1986; Annual rept. Oct. 1, 1985-Mar. 31, 1986, Final rept. Oct. 1, 1983-Mar. 31, 1986. Corporate Author: Medical Coli of Gerogia Augusta Research Institute. Brunt and Klausner, "Growth factors speed wound healing", *Nature Biotechnology*, 6(1): 25-30 (1988).
Reijnen, M.M.P.J., et al., "Prevention of intra-abdominal abscesses and adhesions using a hyaluronic acid solution in a rat peritonitis model." *Arch Surg.* 134: 997-1001 (1999).
Renkens, K., et al., "A Multicenter, Prospective, Randomized Trial Evaluating a New Hemostatic Agent for Spinal Surgery," *Spine*, 26(15): 1645-1650 (2001).
Riley, S., et al. "Percutaneous Liver Biopsy with Plugging of Needle Track: A Safe Method for Use in Patients with Impaired Coagulation," *Lancet*, p. 436 (1984).

(56) References Cited

OTHER PUBLICATIONS

Roda, A., et al., "Protein Microdeposition Using a Conventional Ink-Jet Printer," *BioTechniques*, 28(3): 492-496 (2000).
Romanelli, M., et al., "Exudate Management Made Easy", downloaded from http://www.woundsinternational.com, 6 pgs., (Jan. 29, 2010).
Rosenblatt, J., et al., "Effect of Electrostatic Forces on the Dynamic Rheological Properties of Injectable Collagen Biomaterials," *Biomaterials*, 13: 878-886 (1982).
Rosenblatt, J., et al., "Injectable Collagen as a pH Sensitive Hydrogel," *Biomaterials*, 12: 985-995 (1994).
Ross, J., et al., "Association Between Peridural Scar and Recurrent Radicular Pain After Lumbar Discectomy: Magnetic Resonance Evaluation," *Neurosurgery*, pp. 855-863 (1996).
Rossler, B., et al., "Collagen Microparticles: Preparation and Properties," *Journal of Microencapsulation*, 12: 49-57 (1995).
Sakurabayashi, S., et al., "Clinical evaluation of new hemostatic agent for hemostasis from biopsy wounds in the liver."; Gastroenterological Endoscopy 30:(10) 29 pgs. (Oct. 1988).
Sanfilippo, J.S., et al., "Comparison of avitene, topical thrombin and Gelfoam as sole hemostatic agent in tuboplasties.", *Fertility and Sterility*, 33(3): 311-316 (1980).
San-Galli, F., et al., "Experimental Evaluation of a Collagen-Coated Vicryl Mesh as a Dural Substitute," *Neurosurgery*, 30: 396-401 (1992).
Santomaso, A., et al., "Powder flowability and density rations: the impact of granules packing", *Chemical Engineering Science*, 58: 2857-2874 (2003).
Schramm, V., et al., "Gelfoam Paste Injection for Vocal Cord Paralysis," *The Laryngoscope*, 88: 1268-73 (1978).
Schreiber, M.A., et al., "Achieving Hemostasis with Topical Hemostats: Making Clinically and Economically Appropriate Decisions in the Surgical and Trauma Settings", *AORN Journal*, 94(5): S1-S20 (2011).
Shaffrey, C.I., et al., "Neurosurgical Applications of Fibrin Glue: Augmentation of Dural Closure in 134 Patients," *Neurosurgery*, 26: 207-210 (1990).
Shushan, A., et al., "Hyaluronic acid for preventing experimental postoperative intraperitoneal adhesions.", *Journal of Reproductive Medicine*, 39(5): 398-402 (1994).
Shuxian, M. and Zhili, C., "Clinical Observation of the Treatment of Hemoptysis by Ultrasonic Atomizing Inhalation of Thrombin", *Chinese Journal of Critical Care Medicine*, 16(2): 30 (1996).
Sidman, K., et al., "Biodegradable, Implantable Sustained Release Systems Based on Glutamic Acid Copolymers," *Journal of Membrane Science*, 7: 227-291 (1979).
Sigma-Aldrich Datasheet for "Hank's Balanced Salts," revised Apr. 2007.
Simamora, P., et al., "Controlled delivery of pilocarpine. 2. In-vivo evaluation of Gelfoam® device," *International Journal of Pharmaceutics*, 170(2): 209-214 (1998).
Smith, A., "New and Nonofficial Remedies: Absorbable Gelatin Sponge—Gelfoam—Upjohn," *Council on Pharmacy and Chemistry*, 135(14): p. 921 (1947).
Smith, K., et al., "Delayed Postoperative Tethering of the Cervical Spinal Cord," *Journal of Neurosurgery*, 81: 196-201 (1994).
Solar Biologicals Inc., "Solar-cult sampling products: Premoistened cellulose sponge sampling systems", available at www.solarbiologicals.com/samp-sys.htm (Jul. 25, 2002).
Soules, M.R., et al., "The prevention of postoperative pelvic adhesions: An animal study comparing barrier methods with Dextran 70.", *Am. J. Obstet. Gynecol.*, 143(7): 829-834 (1982).
Spence et al., "Cerebellar capillary hemangioblastoma: its histogenesis studied by organ culture and electron microscopy.", *Cancer*, 35(2): 326-341 (Feb. 1975).
Spotnitz, W. D., et al., "Hemostatus, Sealants, and Adhesives: Components of the Surgical Toolbox," *Transfusion*, 48(7):1502-1516 (2008).
Springorum, H., "Die Verwendung von Kollagenfolien Zur Uberbruckung von Defekten des Gleitgewebes bei Achillotenotomien und Achillessehnenrupturen," *Akt. Traumatol.*, 15: 120-121, English abstract only on p. 120 (1985).
Stief, T. W., "Kallikrein Activates Prothrombin," *Clinical and Applied Thrombosis/Hemostasis*, 14.1:97-98 (2008).
Stricker, A., et al., "Die Verwendung von TissuFoil Membran bei der Sinusbodenaugmentation," *Ellipse*, 17: 1-5 (2001). English abstract only on p. 1.
Stuart Transport medium information sheet [retrieved online on May 27, 2009].
Sugitachi, A., et al., "A Newly Devised Chemo-Embolic Agent, G.T. XIIIADM," Gan. To. Kagaku Ryoho, 12: 1942-1943 (1985). English abstract retrieved from http://www.ncbi.nlm.nih.gov on Jan. 2, 2001.
Sugitachi, A., et al., "Locoregional Therapy in Patients with Malignant Pleural Effusion—Two Different Kinds of 'BAC Therapy'," Gan. To. Kagaku Ryoho, 19: 1640-1643 (1992). English abstract retrieved from http://www.ncbi.nlm.nih.gov on Jan. 3, 2001.
Sugitachi, A., et al., "Preoperative Transcatheter Arterial Chemo-Embolization for Locally Advanced Breast Cancer: Application for New Thrombotic Materials." *Japanese Journal of Surgery*, 13: 456-458 (1992).
Surgiflo® Essential Prescribing Information, Hemostatic Matrix (Made from Absorbable Gelatin Sponge, U.S.P.), 1 page (2005).
Surgiflo® haemostatic matrix FlexTip, MS0009, 84 pages (2007).
Surgiflo® product leaflet, "Surgiflo® Hemostatic Matrix Kit," 5 pages (2012).
Surgiflo® product leaflet, "Surgiflo® Hemostatic Matrix," 12 pages (2009).
Swann, D.A., "Studies on hyaluronic acid—I. The preparation and properties of rooster comb hyaluronic acid", *Biochemica et biophysica acta*, 156: 17-30 (1968).
Taheri, Z., "The Use of Gelfoam Paste in Anterior Cervical Fusion," *Journal of Neurosurgery*, 34: 438 (1971).
Tobin, M., et al., "Plugged Liver Biopsy in Patients with Impaired Coagulation," *Digestive Diseases and Science*, 34: 13-15 (1989).
Tucker, H., "Absorbable Gelatin (Gelfoam) Sponge," Springfield, Illinois, Charles T. Thomas, pp. 3-125 (1965).
Van den Bosch, E., et al., "Gelatin degradation at elevated temperature", *International Journal of Biological Macromolecules*, 32: 129-138 (2003).
Vandelli, M.A., et al., "The effect of the crosslinking time period upon the drug release and the dynamic swelling of gelatin microspheres," *Pharmazie*, 46: 866-869 (1991).
Vander-Salm, T.J., et al., Abstract of "Reduction of sternal infection by application of topical vancomycin.", *J. of Thoracic and Cardiovascular Surgery*, 98(4): 618-622 (1989).
Verhoeven, A.G., et al., "XV. The use of microporous polymeric powders for controlled release drug delivery systems," *Controlled Drug Delivery*. Ch. 15, International Symposium of the Association for Pharmaceutical Technology (APV), Bad Homburg, Nov. 12-14, 1984, pp. 226-237.
Vinas, F., et al., "Evaluation of Expanded Polytetrafluoroethylene (ePTFE) versus Polydioxanone (PDS) for the Repair of Dura Mater Defects," *Neurological Research*, 21: 262-268 (1999).
Wachol-Drewek, Z., et al., "Comparative investigation of drug delivery of collagen implants saturated in antibiotic solutions and a sponge containing gentamicin.", *Biomaterials*, 17: 1733-1738 (1996).
Wallace, D., "The Relative Contribution of Electrostatic Interactions to Stabilization of Collagen Fibrils," *Biopolymers*, 29: 1015-1026 (1990).
Wallace, D., et al., "Injectable Cross-Linked Collagen with Improved Flow Properties," *Journal of Biomedical Materials Research*, 23: 931-945 (1989).
Warren, W., et al., "Dural Repair Using Acellular Human Dermis: Experience with 200 Cases: Technique Assessment," *Neurosurgery*, 46: 1391-1396 (2000).
Wassersug, J.D., M.D., "Use of Human Thrombin in Some Cases of Pulmonary Hemorrhage" *Pulmonary Hemorrhage*, vol. XVII, pp. 354-356 (Mar. 1950).
Weeks, R., "Microscopy of Soft Materials," *Chapter I in Experimental and Computational Techniques in Soft Condensed Matter Physics*, Jeffrey Olafsen, Ed, 2010 (2010).

(56) References Cited

OTHER PUBLICATIONS

West et al., "Efficacy of adhesion barriers: Resorbable hydrogel, oxidized regenerated cellulose and hyaluronic acid.", *The Journal of Reproductive Medicine*, 41(3) 149-154 (1996).

Wiesenthal, A.A., et al., Abstract of "New method for packing the external auditory canal, middle ear space, and mastoid cavities after otologic surgery", *The Journal of Otolaryngology*, 28(5): 260-265 (1999).

Wilkinson, H., et al., "Gelfoam Paste in Experimental Laminectomy and Cranial Trephination," *Journal of Neurosurgery*, 54: 664-667 (1981).

Wu, Y. et al., Abstract of "Design and experimental study of a slow-release antibiotic membrane implant in surgery wound.", *Intern. Des Services de San. Des Forces Armees*; 72(7-9): 194-196 (Sep. 1999).

Xing, Q., et al., "Increasing Mechanical Strength of Gelatin Hydrogels by Divalent Metal Ion Removal", *Sci. Rep.*, 4: 4706: DOI: 10.1038/srep04706(2014).

Xu, T., et al., "Viability and electrophysiology of neural cell structures generated by the inkjet printing method", *Biomaterials*, 27: 3580-3588 (2006).

Xu, T., et al., "Inkjet Printing of Viable Mammalian Cells," *Biomaterials*, 26: 93-99 (2005).

Yaping, G., "Observation and Nursing of the Treatment of Hemoptysis of Pulmonary Tuberculosis by Ultrasonic Atomizing Inhalation of Thrombin", *Journal of Qilu Nursing*, 10(2): 126 (Feb. 2004).

Youwen, W. et al., "Clinical Observation of the Therapeutic Efficacy of the Treatment of 15 Patients with Hemoptysis by Ultrasonic Atomizing Inhalation of Thrombin", *Chengdu Medical Journal*, 30(5): 262 (Oct. 2004).

Yuki, N., et al., "Effects of Endoscopic Variceal Sclerotherapy Using GT XIII on Blood Coagulation Tests and the Renal Kallikrein-Kinin System," Gastroentral. Japan, 25: 561-567 (1990). English abstract retrieved from http://www.ncbi.nlm.nih.gov [retrieved on Jan. 2, 2001].

Ziegelaar, B., et al., "The Characterisation of Human Respiratory Epithelial Cells Cultured on Resorbable Scaffords: First Steps Towards a Tissue Engineered Tracheal Replacement," *Biomaterials*, 23: 1425-1438 (2002).

Ziegelaar, B., et al., "Tissue Engineering of a Tracheal Equivalent, Doctoral Thesis," Munich, Germany, Ludwig Maximilians University, 2004, 25 pages (2004).

Zins, M., et al., "US-Guided Percutaneous Liver Biopsy with Plugging of the Needle Track: A Prospective Study in 72 High-Risk Patients," *Radiology*, 184: 841-843 (1992).

\* cited by examiner

METHOD FOR PREPARING A HAEMOSTATIC COMPOSITION

RELATED APPLICATIONS

This application claims the benefit of U.S. Provisional Application No. 62/669,056, filed on May 9, 2018. The entire teachings of the above application is incorporated herein by reference.

TECHNICAL FIELD

The present disclosure relates to a simplified method for preparing a haemostatic paste composition comprising thrombin, the method comprising the step of reconstituting a dry thrombin directly in a paste, such as a paste comprising a biocompatible polymer. The haemostatic composition comprising thrombin may be prepared from a dry thrombin composition and a paste in a single step operation and be used for treatment of a wound.

BACKGROUND

Protein-based haemostatic materials such as collagen and gelatine are commercially available in solid sponge and loose or unpacked powder form for use in surgical procedures. Mixing of the loose or unpacked powder with a fluid such as saline or a thrombin solution may form a paste or slurry that is useful as a haemostatic composition for use in cases of diffuse bleeding, particularly from uneven surfaces or hard to reach areas, depending on mixing conditions and relative ratios of the materials.

Conventional haemostatic pastes are usually prepared at the point of use by mechanical agitation and mixing of a biocompatible polymer, e.g. gelatine, and a liquid, e.g. a thrombin solution, to provide uniformity of the composition. Mixing to form a paste usually requires extensive mixing, such as kneading or transfer between two syringes.

It is often desired that the haemostatic paste comprises a thrombin component to provide optimal haemostatic effect of the paste. Due to stability reasons, the thrombin component is usually provided as a dry composition separate from the biocompatible polymer component. The dry thrombin is then reconstituted to form a suspension or solution before mixing with the biocompatible polymer. This step of reconstitution of the thrombin component usually takes place immediately prior to mixing with the biocompatible polymer. Reconstitution of thrombin is time consuming and challenging with multi-step syringe handlings involved; factors which are undesirable in an operating room setting with bleedings, as the surgeon will have to abrupt his procedure while waiting for the haemostat to be prepared.

Surgiflo® Haemostatic Matrix (Ethicon) is a kit for producing a haemostatic gelatine paste comprising thrombin, which is prepared by first reconstituting a dry thrombin composition and subsequent transferring a gelatine matrix-thrombin solution mixture back and forth between two connected syringes for a total of at least six passes.

Floseal® Haemostatic Matrix (Baxter) is likewise a kit for producing a haemostatic gelatine paste, requiring initial reconstitution of a dry thrombin composition followed by transfer of the gelatine matrix-thrombin solution mixture back and forth between two connected syringes for a total of at least twenty passes. Once a substantially homogenous paste composition is achieved, the haemostatic pastes can be applied to a bleeding to promote haemostasis by extruding the pastes from the syringe.

Attempts have also been made to provide the biocompatible polymer and the thrombin in dry form in the same syringe, such as described previously in e.g. WO 2011/151400, WO 2011/151384, WO 2011/151386 and WO 2013/185776, the teachings of which are incorporated by reference in their entirety. However, due to the sensitivity of thrombin to the sterilisation methods usually employed in the manufacture of haemostatic products, i.e. ionising radiation and/or ethylene oxide, the sensitivity of thrombin to water and the different physical-chemical properties of thrombin and the polymers usually employed, such as gelatine, it has proven challenging to manufacture such "all-in-one" products so that they retain sufficient thrombin activity during manufacturing, sterilisation and throughout the shelf-life of the product and/or which ensures satisfactory distribution of thrombin in the final reconstituted haemostatic paste product.

As mentioned above, incorporation of thrombin in the haemostatic paste is challenging due to either manufacturing or stability reasons or due to time consuming reconstitution of a dry thrombin composition prior to mixing with the biocompatible polymer. Thus, there is a need in the art for developing novel methods for quick and easy incorporation of thrombin in the haemostatic paste.

SUMMARY

The present disclosure addresses the above problems relating to incorporation of thrombin in haemostatic pastes and provides a method for reconstituting a dry thrombin composition directly in a paste comprising a biocompatible polymer, to generate a haemostatic paste comprising thrombin in a single step operation. Such simple and fast method for preparing a haemostatic composition is highly valuable in the operating room where potential bleeding must be controlled in a fast and efficient manner.

Thus, in one aspect, the present disclosure relates to a method for preparing a haemostatic composition, the method comprising the steps of:
a) providing a dry thrombin composition in a first container;
b) providing a paste comprising a biocompatible polymer in a second container;
c) connecting the first container and the second container using suitable connecting means; and
d) mixing the contents of the containers.

In a second aspect, the present disclosure relates to a method for reconstituting a dry thrombin composition, the method comprising the steps of:
a) providing a dry thrombin composition in a first container;
b) providing a paste comprising a biocompatible polymer in a second container;
c) connecting the first container and the second container using suitable connecting means; and
d) mixing the contents of the containers.

The mixing of the contents of the containers may be performed by transferring the contents of the containers back and forth a number of times, such as less than 20 times, for example less than 15 times, such as less than 10 times, preferably about six times.

The inventors have surprisingly found that such method for reconstituting a dry thrombin composition directly in a paste comprising a biocompatible polymer results in a substantially homogenous distribution of the thrombin in the haemostatic composition. Thus, the present disclosure provides a method for preparing a haemostatic composition comprising thrombin in a fast and simple manner which does not require separate reconstitution of the thrombin component prior to mixing with the biocompatible polymer.

The present disclosure further relates to a haemostatic composition obtainable by the methods as described herein as well as to uses thereof.

Figure 1:
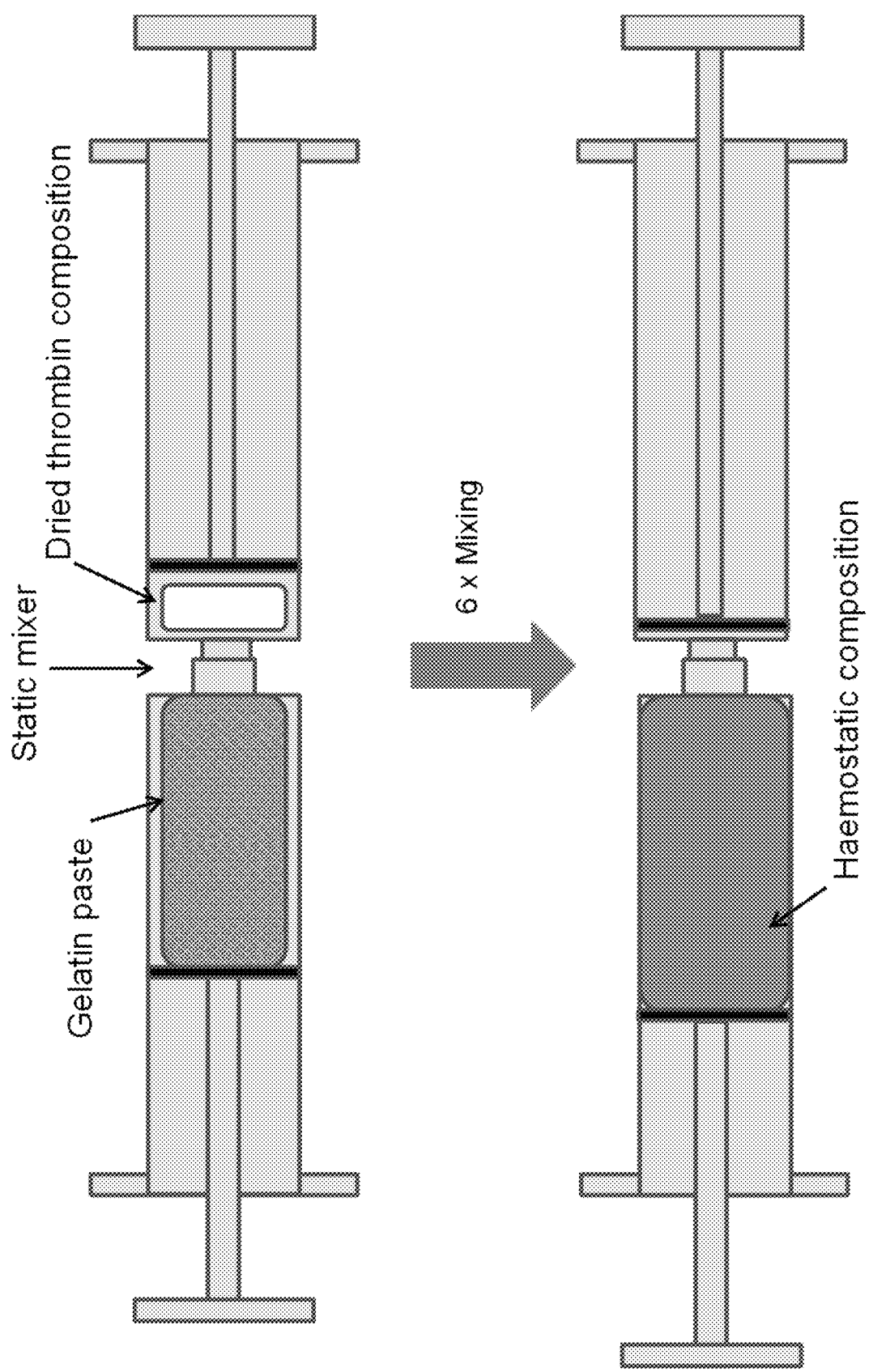
FIG. 1
Figure 2:
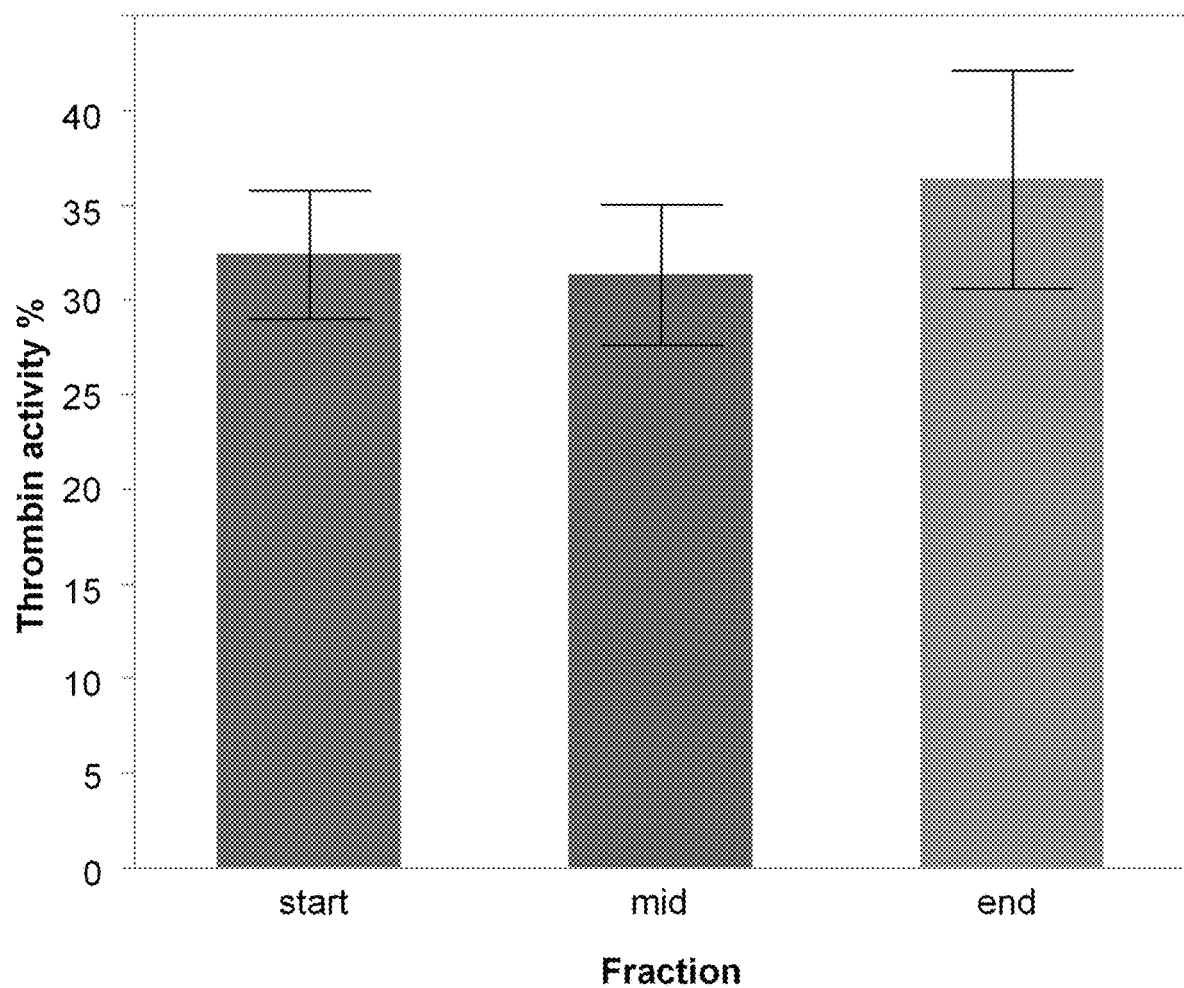

Displays an exemplary setup and method for reconstituting a dry thrombin composition directly in a paste comprising a biocompatible polymer to generate a haemostatic composition. The dry thrombin composition is contained in a first syringe and the paste comprising a biocompatible polymer, here exemplified by a gelatine paste, is contained in a second syringe. The two syringes are interconnected, in this embodiment via a static mixer, and the content of the syringes is transferred back and forth six times to generate the haemostatic composition.

FIG. 2

Displays thrombin activity distribution in the start, mid and end portion of a syringe comprising a haemostatic composition reconstituted using the method of the present disclosure. The mean thrombin activity is given as percentage of the total thrombin activity. The data shows that reconstitution of dry thrombin with a paste yields a haemostatic paste composition having a homogeneous distribution of thrombin. Error bars are constructed using one standard deviation from the mean.

FIG. 3

Displays haemostatic efficacy (Time to Haemostasis (TTH)) of a paste of the present invention (6TM paste) compared to control (Surgiflo mixed with 2 ml thrombin solution) (Mean+/−SEM, n=7). The 6TM paste prepared according to the present invention was found to induce haemostasis faster and more consistently than the control paste.

DEFINITIONS

A "bioactive agent" is any agent, drug, compound, composition of matter or mixture which provides some pharmacologic, often beneficial, effect that can be demonstrated in vivo or in vitro. An agent is thus considered bioactive if it has interaction with or effect on a cell tissue in the human or animal body. As used herein, this term further includes any physiologically or pharmacologically active substance that produces a localized or systemic effect in an individual. Bioactive agents may be a protein, such as an enzyme. Further examples of bioactive agents include, but are not limited to, agents comprising or consisting of an oligosaccharide, a polysaccharide, an optionally glycosylated peptide, an optionally glycosylated polypeptide, an oligonucleotide, a polynucleotide, a lipid, a fatty acid, a fatty acid ester and secondary metabolites. It may be used either prophylactically, therapeutically, in connection with treatment of an individual, such as a human or any other animal. The term "bioactive agent" as used herein does not encompass cells, such as eukaryotic or prokaryotic cells.

"Biocompatible" refers to a material's ability to perform its intended function without eliciting any substantial undesirable local or systemic effects in the host.

"Biologically absorbable" or "resorbable" are terms which in the present context are used to describe that the materials of which the said powder are made can be degraded in the body to smaller molecules having a size which allows them to be transported into the blood stream. By said degradation and absorption the said powder materials will gradually be removed from the site of application. For example, gelatine can be degraded by proteolytic tissue enzymes to absorbable smaller molecules, whereby the gelatine, when applied in tissues, typically is absorbed within about 4-6 weeks and when applied on bleeding surfaces and mucous membranes typically within 3-5 days.

A "gel" is a solid, jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness) and contribute to stickiness (tack). In this way gels are a dispersion of molecules of a liquid within a solid in which the solid is the continuous phase and the liquid is the discontinuous phase. A gel is not a paste or slurry. For example, non-crosslinked gelatine is soluble and forms a gel upon contact with an aqueous medium such as water.

"Haemostasis" is a process which causes bleeding to diminish or stop. Haemostasis occurs when blood is present outside of the body or blood vessels and is the instinctive response for the body to stop bleeding and loss of blood. During haemostasis three steps occur in a rapid sequence. Vascular spasm is the first response as the blood vessels constrict to allow less blood to be lost. In the second step, platelet plug formation, platelets stick together to form a temporary seal to cover the break in the vessel wall. The third and last step is called coagulation or blood clotting. Coagulation reinforces the platelet plug with fibrin threads that act as a "molecular glue". Accordingly, a haemostatic compound is capable of stimulating haemostasis.

"International Unit (IU)". In pharmacology, the International Unit is a unit of measurement for the amount of a substance, based on biological activity or effect. It is abbreviated as IU, UI, or as IE. It is used to quantify vitamins, hormones, some medications, vaccines, blood products, and similar biologically active substances.

A "paste" according to the present disclosure has a malleable, putty-like consistency, such as toothpaste. A paste is a thick fluid mixture of pulverized solid/solid in powder form with a liquid. A paste is a substance that behaves as a solid until a sufficiently large load or stress is applied, at which point it flows like a fluid, i.e. a paste is flowable. Flowables conform efficiently to irregular surfaces upon application. Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes a paste to demonstrate properties of fragile matter. A paste is not a gel/jelly. A "slurry" is a fluid mixture of a powdered/pulverized solid with a liquid, such as water. Slurries behave in some ways like thick fluids, flowing under gravity and being capable of being pumped if not too thick. A slurry may functionally be regarded as a thin, watery paste, but a slurry generally contains more water than a paste. Substantially water-insoluble powder particles, such as cross-linked gelatine particles, will form a paste upon mixing with an aqueous medium.

"Percentage". If nothing else is indicated, the percentage is percentage by weight: % w/w or wt %. Ratios are indicated as weight by weight (w/w).

"Variation in thrombin content". The variation in thrombin content as used herein is defined as the percentage difference in the mean thrombin activity between two fractions of haemostatic composition. The mean thrombin activity is given as thrombin activity of a fraction as a percentage of the total thrombin activity of the full haemostatic composition.

DETAILED DESCRIPTION

The present disclosure relates to a simplified method for preparing a haemostatic paste composition comprising thrombin. The method comprises the step of reconstituting a dry thrombin composition directly in a paste, such as a paste comprising a biocompatible polymer.

The invention thus relates to a method of preparing a haemostatic composition, the method comprising the steps of:
a) providing a dry thrombin composition in a first container;
b) providing a paste comprising a biocompatible polymer in a second container;
c) connecting the first container and the second container using suitable connecting means; and
d) mixing the contents of the containers.

After mixing, the first or the second container (depending on the number of transfers) may be used as a delivery device to deliver the haemostatic composition to tissue.

Thus, the haemostatic composition comprising thrombin may be prepared from a dry thrombin composition and a paste in a single step operation with no need for prior time-consuming and error prone reconstitution of the dry thrombin composition in a solution.

Such simple and fast method for preparing a haemostatic composition is highly valuable in the operating room where potential bleeding must be controlled in a fast and efficient manner.

The advantages of the methods provided in the present disclosure and the haemostatic composition obtained by such methods are numerous and include:
Less time spent preparing the haemostatic composition, e.g. bleeding can be stopped faster.
Decreased risk of compromising the sterility of the haemostatic composition during preparation due to less handling steps.
Decreased risk of making mistakes during preparation due to the simplified preparation of the paste.
Reliable and consistent reconstitution within a short time period.
Avoids the time-consuming and error-prone thrombin dilution steps of standard haemostatic composition preparations.
Minimises Operation Room costs since preparation of the currently described product is so simple and fast that there is no reason to pre-prepare haemostatic flowables before surgery which may not be used.
Increased flexibility to add an aqueous medium to the paste in order to modify the consistency of the final mixed composition.
All of the above factors lead to increased patient safety.

Dry Thrombin Composition

The present disclosure relates to a method for reconstituting a dry thrombin composition directly in a paste.

Thrombin is a "trypsin-like" serine protease protein that in humans is encoded by the F2 gene. Prothrombin (coagulation factor II) is proteolytically cleaved to form thrombin in the coagulation cascade, which ultimately results in the stemming of blood loss. Thrombin in turn acts as a serine protease that converts soluble fibrinogen into insoluble strands of fibrin, as well as catalyzing many other coagulation-related reactions. In the blood coagulation pathway, thrombin acts to convert factor XI to XIa, VIII to VIIIa, V to Va, and fibrinogen to fibrin.

In one embodiment, the thrombin is human thrombin.

In one embodiment, the thrombin is recombinant human thrombin.

In other embodiments, the origin of the thrombin is from a mammal other than human, such as bovine thrombin.

In one embodiment, thrombin is in the form of prothrombin.

The dry thrombin composition may be prepared by any methods known to the skilled person and is usually provided in sterile form. Thus, in one embodiment the dry thrombin composition is sterile.

In one embodiment, the dry thrombin composition is prepared by spray-drying or freeze-drying.

In a preferred embodiment, the dry thrombin composition is prepared by freeze-drying In one embodiment, the dry thrombin composition comprises less than 2% water, such as less than 1% water.

The amount of thrombin in the haemostatic composition should be sufficient to ensure effective haemostasis. In one embodiment the final concentration of thrombin in the haemostatic composition is in the range of about 50 IU/mL to about 1000 IU/mL, for example 100 IU/mL to about 500 IU/mL, such as about 150 IU/mL to about 450 IU/mL, for example about 200 IU/mL to about 400 IU/mL, such as about 200 IU/mL to about 300 IU/mL.

The dry thrombin composition may optionally comprise one or more hydrophilic agent(s), such as for example one or more polyol(s) and/or one or more poly(ethylene glycol)(s) (PEGs).

In one embodiment, the dry thrombin composition comprises one or more further bioactive agent(s). Such one or more bioactive agent(s) may be able to stimulate haemostasis, wound healing, bone healing, tissue healing and/or tendon healing.

In one embodiment, the dry thrombin composition optionally comprises one or more extrusion enhancer(s), such as for example albumin. The use of extrusion enhancers to improve extrudability of haemostatic pastes is e.g. described in WO 2015/086028, which is hereby incorporated in its entirety.

Paste Comprising Biocompatible Polymer

The dry thrombin composition of the disclosure is reconstituted directly in a paste, such as a paste comprising a biocompatible polymer.

The biocompatible polymer of the present disclosure may be a biologic or a non-biologic polymer. Suitable biologic polymers include proteins, such as gelatine, collagen, albumin, hemoglobin, casein, fibrinogen, fibrin, fibronectin, elastin, keratin, and laminin; or derivatives or combinations thereof. Particularly preferred is the use of gelatine or collagen, more preferably gelatine. Other suitable biologic polymers include polysaccharides, such as glycosaminoglycans, starch derivatives, xylan, cellulose derivatives, hemicellulose derivatives, agarose, alginate, and chitosan; or derivatives or combinations thereof. Suitable non-biologic polymers will be selected to be degradable by either of two mechanisms, i.e. (1) break down of the polymeric backbone or (2) degradation of side chains which result in aqueous solubility. Exemplary nonbiologic polymers include synthetics, such as polyacrylates, polymethacrylates, polyacrylamides, polyvinyl resins, polylactide-glycolides, polycaprolactones, and polyoxyethylenes; or derivatives or combinations thereof. Also combinations of different kinds of polymers are possible.

In one embodiment, the biocompatible polymer is biologically absorbable. Examples of suitable biologically absorbable materials include gelatine, collagen, chitin, chitosan, alginate, cellulose, oxidised cellulose, polyglycolic acid, polyacetic acid and combinations thereof. It will be understood that various forms thereof, such as linear or cross-linked forms, salts, esters and the like are also contemplated for the present disclosure. In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means.

In a preferred embodiment the biocompatible polymer is cross-linked. Cross-linking usually renders the polymer substantially insoluble in an aqueous medium. In one embodiment, the biocompatible polymer consists of powder particles which are substantially insoluble in an aqueous medium. Any suitable cross-linking methods known to a person of skill may be used including both chemical and physical cross-linking methods.

In one embodiment of the present disclosure the polymer has been cross-linked by physical means, such as by dry heat. The dry heat treatment is usually performed at temperatures between 100° C. and 250° C., such as about 110° C. to about 200° C. In particular the temperature may be in the range of 110-160° C., e.g. in the range of 110-140° C., or in the range of 120-180° C., or in the range of 130-170° C., or in the range of 130-160° C., or in the range of 120-150° C. The period of time for cross-linking may be optimised by a skilled person and is normally a period between about 10 minutes to about 12 hours, such as about 1 hour to about 10 hours, for example between about 2 hours to about 10 hours, such as between about 4 hours to about 8 hours, for example between about 5 hours to about 7 hours, such as about 6 hours.

In another embodiment, the polymer has been cross-linked by chemical means, i.e. by exposure to a chemical cross-linking agent. Examples of suitable chemical cross-linking agents include but are not limited to aldehydes, in particular glutaraldehyde and formaldehyde, acyl azide, carbodiimides, hexamethylene diisocyanate, polyether oxide, 1,4-butanedioldiglycidyl ether, tannic acid, aldose sugars, e.g. D-fructose, genipin and dye-mediated photo-oxidation. Specific compounds include but are not limited to 1-(3-dimethylaminopropyl)-3-ethylcarbodiimide hydrochloride (EDC) and dithiobis(propanoic dihydrazide) (DTP).

In one embodiment, the biocompatible polymer particles used for the preparation of the paste according to the present disclosure may be obtained from cross-linked sponges of e.g. gelatine or collagen, in particular cross-linked sponges of gelatine (such as the commercially available Spongostan® sponges and Surgifoam® sponges). The cross-linked sponges are micronized by methods known in the art to obtain a cross-linked biocompatible polymer in powder form, such as by rotary bed, extrusion, granulation and treatment in an intensive mixer, or milling (e.g. by using a hammer mill or a centrifugal mill). The cross-linked biocompatible polymer in powder form is then mixed with an amount of aqueous medium to provide a paste of a desirable consistency.

Spongostan®/Surgifoam® available from Ethicon is a gelatine based cross-linked absorbable haemostatic sponge. It absorbs >35 g of blood/g and within 4-6 weeks it is completely absorbed in the human body.

In one embodiment, the paste comprising a biocompatible polymer comprises cross-linked gelatine particles obtained from a micronized porous gelatine sponge, which has been cross-linked by dry heat treatment.

Micronized porous gelatine sponges may be prepared by mixing an amount of soluble gelatine with an aqueous medium in order to create a foam comprising a discontinuous gas phase, drying said foam and crosslinking the dried foam by exposure to dry heat. The obtained cross-linked sponge can be micronized by methods known in the art. The gelatine foam usually has a gelatine concentration from about 1% to 70% by weight, usually from 3% to 20% by weight. Drying is usually performed at about 20° C. to about 40° C. for about 5 to 20 hours. The dried foam is usually cross-linked by exposure to a temperature of about 110° C. to about 200° C. for about 15 minutes to about 8 hours, such as at about 150° C. to about 170° C. for about 5 to 7 hours.

In one embodiment, the biocompatible polymer particles used for the preparation of the paste according to the present disclosure are obtained from cross-linked gels of e.g. gelatine or collagen, in particular cross-linked gelatine gels. The cross-linked gels may be micronized as described above. The cross-linked biocompatible polymer in powder form is then mixed with an amount of aqueous medium to provide a paste of a desirable consistency.

In one embodiment, the paste comprising a biocompatible polymer comprises cross-linked gelatine particles obtained from a micronized gelatine gel, which has been cross-linked by dry heat treatment.

In one embodiment, the paste comprising a biocompatible polymer comprises or consists of cross-linked gelatine particles obtained from a gelatine hydrogel. A gelatine hydrogel may be prepared by dissolving an amount of gelatine in an aqueous buffer to form a non-cross-linked hydrogel, typically having a solids content from 1% to 70% by weight, usually from 3% to 10% by weight. The gelatine may be cross-linked, for example by exposure to either glutaraldehyde (e.g. 0.01% to 0.05% w/w, overnight at 0° C. to 15° C. in aqueous buffer), sodium periodate (e.g. 0.05 M, held at 0° C. to 15° C. for 48 hours) or 1-ethyl-3-(3-dimethylaminopropyl) carbodiimide (EDC) (e.g. 0.5% to 1.5% w/w, overnight at room temperature), or by exposure to about 0.3 to 3 megarads of gamma or electron beam radiation. The resulting crosslinked hydrogels may be fragmented and dried to obtain a gelatine powder. Alternatively, gelatine particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). When cross-linking with glutaraldehyde, the cross-links are formed via Schiff bases which may be stabilized by subsequent reduction, e.g. by treatment with sodium borohydride. After cross-linking, the resulting granules may be washed in water and optionally rinsed in an alcohol and dried to obtain a gelatine powder. In one embodiment, cross-linked gelatine particles are prepared essentially as described in U.S. Pat. No. 6,066,325.

In one embodiment, the paste comprises a biocompatible polymer in a content of about 7% to 20%, such as about 8% to 18%, for example about 10% to 16%, such as about 11%-15%, for example about 12%-14%.

In one embodiment, the paste comprises a biocompatible polymer in a content of about 7% to 20%, such as about 7% to 18%, for example about 7% to 16%, such as about 7% to 14%, for example about 7% to 13%, such as about 7% to 12%, for example about 7% to 11%, such as about 7% to 10%, for example about 7% to 9%.

In one embodiment, the paste comprises a biocompatible polymer in a content of about 7% to 20%, such as about 10% to 20%, for example about 11% to 20%, such as about 12% to 20%, for example about 13% to 20%, such as about 14% to 20%, for example about 15% to 20%, such as about 17% to 20%, for example about 19% to 20%.

In one embodiment, the paste comprises a biocompatible polymer in a content of about 10% to 20%, such as about 10% to 18%, for example about 10% to 16%, such as about 10% to 15%.

The paste comprising a biocompatible polymer may further comprise one or more hydrophilic agent(s), such as for example one or more polyol(s) and/or one or more poly(ethylene glycol)(s) (PEG).

In one embodiment, the paste comprising a biocompatible polymer comprises one or more further bioactive agent(s). Such one or more bioactive agent(s) may be able to stimulate haemostasis, wound healing, bone healing, tissue healing and/or tendon healing.

In one embodiment, the paste comprising a biocompatible polymer comprises one or more extrusion enhancer(s), such as for example albumin.

In one embodiment, the paste comprising a biocompatible polymer comprises one or more antimicrobial agents, such as one or more antibacterial agents.

In one embodiment, the paste comprising a biocompatible polymer comprises benzalkonium chloride.

The paste comprising a biocompatible polymer as described herein may be prepared according to techniques known in the art. Accordingly, the paste comprising a biocompatible polymer may be prepared by mixing of a biocompatible polymer powder with an aqueous medium to generate said paste.

The paste comprising a biocompatible polymer is usually provided in sterile form. Thus, in one embodiment the paste comprising a biocompatible polymer is sterile.

The paste comprising a biocompatible polymer further comprises an aqueous medium, such as for example water, saline, a calcium chloride solution or a buffered aqueous medium.

Aqueous Medium

An aqueous medium may be used in the present disclosure for preparing the paste comprising a biocompatible polymer.

The aqueous medium of the present disclosure may be any aqueous medium suitable for preparing a paste known to a person of skill, e.g. water, saline or a buffered aqueous medium. The water may be WFI (Water For Injection). It is important that the aqueous medium is selected so that the reconstituted paste product is essentially isotonic when intended for use on a human or animal subject, such as for haemostatic and/or wound healing purposes. The aqueous medium is preferably sterile.

The aqueous medium of the present disclosure is in one embodiment a saline solution.

In one embodiment, the aqueous medium is a calcium chloride solution.

In other embodiments, the aqueous medium is water.

The aqueous medium may also be a buffered aqueous medium suitable for use in a haemostatic paste. Any suitable buffering agent known to a person of skill may be used, such as one or more buffering agents selected from the group consisting of: Sodium citrate; Citric acid, Sodium citrate; Acetic acid, Sodium acetate; $K_2HPO_4$, $KH_2PO_4$; $Na_2HPO_4$, $NaH_2PO_4$; CHES; Borax, Sodium hydroxide; TAPS; Bicine; Tris; Tricine; TAPSO; HEPES; TES; MOPS; PIPES; Cacodylate; SSC; IVIES, or others. The pH of the buffered aqueous medium should be suitable for creating a haemostatic paste intended for human use and can be determined by the skilled person.

Thus, in one embodiment the paste comprising a biocompatible polymer comprises an aqueous medium selected from the group consisting of water, saline, a calcium chloride solution and a buffered aqueous medium.

In one embodiment, the paste comprising a biocompatible polymer comprises between about 60% to about 95% of water, for example about 70% to about 90% of water, such as between about 75% to about 90% of water, for example between about 80% to about 90% of water.

The aqueous medium may comprise one or more hydrophilic agent(s), such as for example one or more polyol(s) or one or more poly(ethylene glycol)(s) (PEG).

In one embodiment, the aqueous medium comprises one or more further bioactive agent(s). Such one or more bioactive agent(s) may be able to stimulate haemostasis, wound healing, bone healing, tissue healing and/or tendon healing.

In one embodiment, the aqueous medium comprises one or more extrusion enhancer(s), such as for example albumin.

Hydrophilic Compounds

In one embodiment, the haemostatic composition comprises one or more hydrophilic compounds. Hydrophilic compounds usually contain polar or charged functional groups, rendering them soluble in water. Inclusion of one or more hydrophilic compounds in the haemostatic composition of the present disclosure is believed to have a beneficial effect on thrombin stability and may improve reconstitution efficiency of the dry thrombin composition. Hydrophilic compounds may also improve consistency of the haemostatic composition.

In one embodiment, the hydrophilic compound is a hydrophilic polymer. The hydrophilic polymer may be natural or synthetic, linear or branched, and have any suitable length.

In one embodiment, the hydrophilic polymer is selected from the group consisting of Polyethylenimine (PEI), Poly(ethylene glycol) (PEG), Poly(ethylene oxide), Poly(vinyl alcohol) (PVA), Poly(styrenesulfonate) (PSS), Poly(acrylic acid) (PAA), Poly(allylamine hydrochloride) and Poly(vinyl acid). In one embodiment, the hydrophilic compound is PEG.

In one embodiment, the hydrophilic compound is selected from the group consisting of Cetylpyridinium Chloride, Docusate Sodium, Glycine, Hypromellose, Phthalate, Lechitin, Phospholipids, Poloxamer, Polyoxyethylene Alkyl Ethers, Polyoxyethylene Castor Oil Derivatives, Polyoxyethylene Sorbitan Fatty Acid Esters, Polyoxyethylene Stearates, Polyvinyl Alcohol, Sodium Lauryl Sulfate, Sorbitan Esters (Sorbitan Fatty Acid Esters) and Tricaprylin.

In a preferred embodiment, the hydrophilic compound is a polyol. Thus, according to one embodiment of the invention, one or more polyols may be included in the haemostatic composition. Polyols may enhance the reconstitution rate of the dry thrombin composition, stabilize thrombin activity and play a role in ensuring an optimal consistency of the haemostatic composition.

A polyol as defined herein is a compound with multiple hydroxyl functional groups. Polyols include sugars (mono-, di- and polysaccharides), sugar alcohols and derivatives thereof. Especially preferred are sugar alcohols.

Monosaccharides include but are not limited to glucose, fructose, galactose, xylose and ribose.

Disaccharides include but are not limited to sucrose (saccharose), lactulose, lactose, maltose, trehalose and cellobiose.

Polysaccharides include but are not limited to starch, glycogen, cellulose and chitin.

A sugar alcohol, also known as a polyalcohol is a hydrogenated form of carbohydrate, whose carbonyl group (aldehyde or ketone, reducing sugar) has been reduced to a primary or secondary hydroxyl group (hence the alcohol). Sugar alcohols have the general formula $H(HCHO)_{n+1}H$, whereas sugars have $H(HCHO)_nHCO$. Some common sugar alcohols which may be used in the method of the present disclosure include but are not limited to: Glycol (2-carbon), Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Dulcitol (6-carbon), Fucitol (6-carbon), Iditol (6-carbon), Inositol (6-carbon; a cyclic sugar alcohol), volemitol (7-carbon), Isomalt (12-carbon), Maltitol (12-carbon), Lactitol (12-carbon), Polyglycitol.

In one embodiment, the haemostatic composition comprises a single hydrophilic compound, such as a single polyol.

In one embodiment of the invention, the haemostatic composition comprises more than one hydrophilic compound, such as two, three, four, five, six or even more different hydrophilic compounds.

In a preferred embodiment, the hydrophilic compound is a polyol.

In one embodiment of the invention, the haemostatic composition comprises two polyols, for example mannitol and glycerol or trehalose and a glycol.

In one embodiment of the invention, the haemostatic composition comprises one or more sugar alcohols, such as one or more sugar alcohols selected from the group consisting of Glycol, Glycerol, Erythritol, Threitol, Arabitol, Xylitol, Ribitol, Mannitol, Sorbitol, Dulcitol, Fucitol, Iditol, Inositol, volemitol, Isomalt, Maltitol, Lactitol, Polyglycitol.

In one embodiment, the haemostatic composition comprises one or more sugar alcohols and one or more sugars, such as one sugar alcohol and one sugar.

In one embodiment, the haemostatic composition comprises one sugar alcohol and optionally one or more additional hydrophilic compounds, such as one or more polyols, which may be either sugar alcohols or sugars.

In one embodiment, the haemostatic composition does not comprise a sugar as the only polyol.

In one embodiment of the invention, the haemostatic composition comprises mannitol.

In one embodiment of the invention, the haemostatic composition comprises sorbitol.

In one embodiment of the invention, the haemostatic composition comprises glycerol.

In one embodiment of the invention, the haemostatic composition comprises trehalose.

In one embodiment of the invention, the haemostatic composition comprises glycol, such as propylene glycol.

In one embodiment of the invention, the haemostatic composition comprises xylitol.

In one embodiment of the invention, the haemostatic composition comprises maltitol.

In one embodiment of the invention, the haemostatic composition comprises sorbitol.

In one embodiment the haemostatic composition comprises from about 1% to about 20% of one or more hydrophilic compounds, for example from about 1% to about 15% of one or more hydrophilic compounds, such as from about 1% to about 10% of one or more hydrophilic compounds, for example from about 1% to about 7% of one or more hydrophilic compounds, such as from about 1% to about 5% of one or more hydrophilic compounds, such as from about 2% to about 5% of one or more hydrophilic compounds, for example from about 3% to about 5% of one or more hydrophilic compounds.

In one embodiment the hydrophilic compound of the present disclosure is not poly(ethylene glycol) (PEG).

The hydrophilic compound may be a component of the dry thrombin composition, a component of the paste comprising a biocompatible polymer and/or be incorporated into the haemostatic composition in a separate step after reconstitution of the dry thrombin composition.

In one embodiment, the one or more hydrophilic compound(s) is a component of the dry thrombin composition.

In one embodiment, the one or more hydrophilic compound(s) is a component of the paste comprising a biocompatible polymer.

In one embodiment, the one or more hydrophilic compound(s) is incorporated into the haemostatic composition in a separate step after reconstitution of the dry thrombin composition.

Preferably, the hydrophilic compound(s) is included in either the thrombin component or the paste component to avoid further mixing steps to produce the haemostatic composition.

Further Bioactive Agents

In one embodiment of the invention, the haemostatic composition comprises one or more further bioactive agents capable of stimulating haemostasis, wound healing, bone healing, tissue healing and/or tendon healing. The one or more bioactive agents may be a component of the dry thrombin composition, the paste comprising a biocompatible polymer and/or be incorporated into the haemostatic composition in a separate step after reconstitution of the dry thrombin composition. Preferably, such bioactive agents are included in either the dry thrombin composition or in the paste comprising a biocompatible polymer to avoid further mixing steps. It is essential that the bioactive agent retains its bioactivity during storage and reconstitution, i.e. that the agent has retained its biological function in the final haemostatic composition. Many bioactive agents are unstable in solution, particularly enzymes and other proteins that may be degraded or lose their secondary structure when water is present.

The one or more further bioactive agents can be e.g. fibrinogen, fibrinogen in combination with Factor XIII, or fibrinogen and Factor XIII in combination with tranexamic acid.

In one embodiment, the haemostatic composition comprises one or more further bioactive agents that stimulate bone and/or tendon and/or tissue healing such as one or more growth factors selected from the group consisting of matrix metalloproteinases (MMPs), insulin-like growth factor 1 (IGF-I), platelet-derived growth factor (PDGF), vascular endothelial growth factor (VEGF), basic fibroblast growth factor (bFGF) and transforming growth factor beta (TGF-β).

In one embodiment, the haemostatic composition comprises one or more Bone Morphogenetic Proteins (BMPs). Bone morphogenetic proteins (BMPs) are a subgroup of the TGF-β superfamily. Bone Morphogenetic Proteins (BMPs) are a group of growth factors also known as cytokines and as metabologens. Originally discovered by their ability to induce the formation of bone and cartilage, BMPs are now considered to constitute a group of pivotal morphogenetic signals, orchestrating tissue architecture throughout the body.

In one embodiment, the haemostatic composition comprises one or more matrix metalloproteinases (MMPs). MMPs are zinc-dependent endopeptidases. MMPs have a very important role in the degradation and remodeling of the extracellular matrix (ECM) during the healing process after an injury. Certain MMPs including MMP-1, MMP-2, MMP-8, MMP-13, and MMP-14 have collagenase activity, meaning that, unlike many other enzymes, they are capable of degrading collagen I fibrils.

These growth factors all have different roles during the healing process. IGF-1 increases collagen and proteoglycan production during the first stage of inflammation, and PDGF is also present during the early stages after injury and promotes the synthesis of other growth factors along with the synthesis of DNA and the proliferation of cells. The three isoforms of TGF-β (TGF-β1, TGF-β2, TGF-β3) are known to play a role in wound healing and scar formation. VEGF is well known to promote angiogenesis and to induce endothelial cell proliferation and migration.

In one embodiment, the haemostatic composition of the present disclosure comprises flakes or particles of extracelluar matrix (ECM). ECM is the extracellular part of animal tissue that usually provides structural support to the animal cells in addition to performing various other important functions. ECM has been shown to have very beneficial effect in healing as it facilitates functional tissue regeneration.

The variety of further bioactive agents that can be used in conjunction with the haemostatic composition of the invention is vast. In general, bioactive agents which may be administered via the haemostatic composition of the invention include, without limitation, antiinfectives, such as antibiotics and antiviral agents; analgesics and analgesic combinations; antihelmintics; antiarthritics; anticonvulsants; antidepressants; antihistamines; antiinflammatory agents; antimigraine preparations; antineoplastics; antiparkinsonism drugs; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; hormones, such as estradiol and other steroids, including corticosteroids; immunosuppressives; muscle relaxants; parasympatholytics; psychostimulants; naturally derived or genetically engineered proteins, polysaccharides, glycoproteins, or lipoproteins; oligonucleotides, antibodies, antigens, cholinergics, chemotherapeutics, radioactive agents, osteoinductive agents, cystostatics heparin neutralizers, procoagulants and haemostatic agents, such as prothrombin, thrombin, fibrinogen, fibrin, fibronectin, heparinase, Factor X/Xa, Factor VII/VIIa, Factor VIII/VIIIa, Factor IX/IXa, Factor XI/XIa, Factor XII/XIIa, Factor XIII/XIIIa, tissue factor, batroxobin, ancrod, ecarin, von Willebrand Factor, platelet surface glycoproteins, vasopressin, vasopressin analogs, epinephrine, selectin, procoagulant venom, plasminogen activator inhibitor, platelet activating agents and synthetic peptides having haemostatic activity.

In one embodiment, the one or more further bioactive agent(s) is a component of the dry thrombin composition.

In one embodiment, the one or more further bioactive agent(s) is a component of the paste comprising a biocompatible polymer.

In one embodiment, the one or more further bioactive agent(s) is incorporated into the haemostatic composition in a separate step after reconstitution of the dry thrombin composition.

Further Compounds

The haemostatic composition of the invention may further comprise one or more of the following: DMSO (dimethyl sulfoxide) and/or 2-Methyl-2,4-pentanediol (MPD).

In one embodiment, the haemostatic composition of the present disclosure comprises one or more antimicrobial agents, such as one or more antibacterial agents.

In one embodiment, the haemostatic composition of the present disclosure comprises benzalkonium chloride.

In one embodiment, the haemostatic composition of the present disclosure does not comprise an antimicrobial agent.

In one embodiment, the haemostatic composition further comprises an extrusion enhancer, i.e. a compound capable of facilitating extrusion of a paste from a syringe.

It has previously been shown that the provision of certain extrusion enhancers, such as albumin in an appropriate amount, enables the use of higher gelatine concentrations as it decreases the amount of force needed to extrude the gelatine paste composition from e.g. a syringe. The use of higher gelatine concentrations may in turn improve the haemostatic properties of such products. It is necessary to provide the extrusion enhancers in appropriate amounts. The amounts are preferably high enough so as to obtain the extrusion effect, i.e. to enable a flowable paste even for relatively high amounts of the biocompatible polymer, e.g. cross-linked gelatine, so that the haemostatic composition can be accurately applied by a surgeon using e.g. a syringe comprising an applicator tip; on the other hand, the amounts shall be as low as to prevent potential negative functional properties of the haemostatic composition.

The extrusion enhancer is preferably albumin, especially human serum albumin.

In the haemostatic composition of the present invention, the extrusion enhancer, such as albumin, is present in an amount of between about 0.1% to about 10%, such as between about 0.2% to about 8%, for example between about 0.3% to about 7%, preferably between about 0.5% to about 5%, such as between about 1% to about 4%.

In one embodiment, the haemostatic composition of the present invention comprises trace amounts of albumin, such as less than 0.1%, for example less than 0.01%, such as less than 0.001%, for example less than 0.0001%.

The one or more further compound(s) may be a component of the dry thrombin composition, a component of the paste comprising a biocompatible polymer and/or be incorporated into the haemostatic composition in a separate step after reconstitution of the dry thrombin composition.

In one embodiment, the one or more further compound(s) is a component of the dry thrombin composition.

In one embodiment, the one or more further compound(s) is a component of the paste comprising a biocompatible polymer.

In one embodiment, the one or more further compound(s) is incorporated into the haemostatic composition in a separate step after reconstitution of the dry thrombin composition.

Making the Haemostatic Composition/Reconstitution of Dry Thrombin Composition

The present disclosure relates to a method for reconstituting a dry thrombin composition directly in a paste to generate a haemostatic composition suitable for use in the treatment of a wound; particularly for haemostatic purposes.

Thus, in one embodiment, a method of preparing a haemostatic composition is provided, the method comprising the steps of:
a) providing a dry thrombin composition in a first container;
b) providing a paste comprising a biocompatible polymer in a second container;
c) connecting the first container and the second container using suitable connecting means; and
d) mixing the contents of the containers In one embodiment, a method for reconstituting a dry thrombin composition is provided, the method comprising the steps of:
a) providing a dry thrombin composition in a first container;
b) providing a paste comprising a biocompatible polymer in a second container;
c) connecting the first container and the second container using suitable connecting means; and
d) mixing the contents of the containers.

The containers are usually syringes, more preferably interconnectable syringes.

In one embodiment, the suitable connecting means comprises a static mixer. Said static mixer may provide the ability to mix air into the paste during mixing. The dimensions of the static mixer may influence the consistency of the haemostatic composition and the ability to mix air into the haemostatic composition.

In one embodiment, the suitable connecting means comprises a connector portion of a standard type, such as a Luer lock or Luer slip connector. The dimensions of the Luer lock or Luer slip connection may influence the consistency of the haemostatic composition and the ability to mix air into the haemostatic composition.

The mixing is performed by transferring the content of the containers back and forth a number of times.

In one embodiment, the number of transfers is less than 20 times, for example less than 15 times, such as less than 12 times, for example less than 10 times, such as less than 6 times.

In one embodiment, the number of transfers is less than 10, for example less than 9, such as less than 8 times, for example less than 7 times, such as less than 6 times, for example less than 5 times.

In one embodiment, the number of transfers is less than 8.

In a preferred embodiment, the number of transfers is about 6 times or less.

Mixing with 6 transfers can be performed as follows: The mixing is initiated by transfer of the paste comprising a biocompatible polymer into the first container holding the dry thrombin composition. Thus, the first transfer is characterized in the transfer of the paste comprising a biocompatible polymer from the second container into the first container. The second transfer is characterized in the transfer of the thrombin and paste mixture, resulting from the first transfer, from the first container into the second container, initially holding the paste comprising a biocompatible polymer. The third transfer is characterized in the transfer of the thrombin and paste mixture, resulting from the second transfer, from the second container into the first container. The fourth transfer is characterized in the transfer of the thrombin and paste mixture, resulting from the third transfer, from the first container into the second container. The fifth transfer is characterized in the transfer of the thrombin and paste mixture, resulting from the fourth transfer, from the second container into the first container. The sixth and final transfer is characterized in the transfer of the thrombin and paste mixture, resulting from the fifth transfer, from the first container into the second container.

In one embodiment, more than six transfers between the first and second containers are used for reconstituting the dry thrombin composition in the paste.

In one embodiment, the final transfer is characterized in the transfer of the thrombin and paste mixture from the first container into the second container. The resulting haemostatic composition may then be applied directly from said second container onto a site of treatment, e.g. onto a bleeding wound. An applicator tip may in some embodiments be fitted to the syringe and employed as described previously.

The mixing of the dry thrombin composition and the paste comprising a biocompatible polymer result in substantially homogenous distribution of thrombin in the haemostatic composition.

The Haemostatic Composition

The haemostatic composition of this disclosure is prepared by reconstituting a dry thrombin composition directly in a paste comprising a biocompatible polymer. The reconstitution of the paste may be performed by methods as described herein. The haemostatic composition has a substantially homogenous distribution of thrombin in the haemostatic composition.

In one embodiment, the homogenous distribution of thrombin is characterized by a variation in thrombin content throughout the haemostatic composition of less than 20%, for example less than 10%, such as less than 5%, for example less than 4%, such as less than 3%, for example less than 2%, such as less than 1%. The variation in thrombin content may be measured as difference in thrombin activity or concentration between different fractions of the haemostatic paste in the container, such as for example between the start fraction of a syringe, the mid fraction of a syringe or the end fraction of a syringe.

In one embodiment the variation in thrombin content throughout the haemostatic composition is less than 10%.

In one embodiment the variation in thrombin content throughout the haemostatic composition is less than 5%.

In one embodiment the variation in thrombin content throughout the haemostatic composition is less than 4%.

In one embodiment the variation in thrombin content throughout the haemostatic composition is less than 3%.

In one embodiment the variation in thrombin content throughout the haemostatic composition is less than 2%.

In one embodiment the variation in thrombin content throughout the haemostatic composition is less than 1%.

The haemostatic composition obtained by the methods described herein is preferably a flowable composition. The haemostatic composition obtained by the methods described herein is suitable for use in haemostasis and/or wound healing.

The haemostatic composition may comprise one or more hydrophilic agent(s), such as for example one or more polyol(s) or one or more poly(ethylene glycol)(s) (PEG).

In one embodiment, the haemostatic composition comprises one or more further bioactive agent(s) besides thrombin. Such one or more bioactive agent(s) may be able to stimulate haemostasis, wound healing, bone healing, tissue healing and/or tendon healing.

In one embodiment, the haemostatic composition comprises one or more extrusion enhancer(s), such as for example albumin.

The haemostatic composition may be obtained by any method of reconstitution of a dry thrombin composition as described herein.

In one embodiment, the haemostatic composition has a consistency within the range of about 100 g×sec to about 10,000 g×sec, such as from about 500 g×sec to about 5000 g×sec, for example from about 1000 g×sec to about 3000 g×sec, such as from about 1500 g×sec to about 2000 g×sec.

In one embodiment, the haemostatic composition has a consistency of less than about 5000 g×sec, for example less than about 4000 g×sec, such as less than about 3000 g×sec, for example less than about 2000 g×sec.

Containers

Any suitable containers known to a person of skill may be used for preparing the haemostatic composition, such as vials, jars, tubes, trays, cartridges or syringes.

The dry thrombin composition is provided in a first container and the paste comprising a biocompatible polymer is provided in a second container.

The first and the second containers may be made from any suitable material such as plastic, glass, ceramic, plastic or metal, such as stainless steel. Examples of suitable plastic materials include but are not limited to polyethylene, polypropylene, polystyrene, polyvinyl chloride, and polytetrafluoroethylene (PTFE).

In one embodiment, the dry thrombin composition is provided in a first container which may be selected from a syringe, a vial, a jar, a tube, a tray, or a cartridge.

In a preferred embodiment said first container holding the dry thrombin composition is a medical delivery device suitable for dispensing flowable haemostatic compositions to a patient in need thereof, such as a syringe.

The first container is usually made from a material suitable for chemical surface sterilisation without influencing the content of the container. For example, said first container may be made from a material which is impermeable to ethylene oxide, such as for example made from metal, glass or a plastic which is impermeable to ethylene oxide.

The dry thrombin composition may preferably be provided in a glass container, thus allowing sterilisation of said container using ethylene oxide gas. In one embodiment, said first container is a glass syringe. In one embodiment, said first container is a syringe having a glass insert holding the dry thrombin.

In one embodiment, the paste comprising a biocompatible polymer is provided in a second container which may be selected from a syringe, a vial, a jar, a tube, a tray, or a cartridge. The paste comprising a biocompatible polymer may be prepared by methods known in the art, such as by mixing of a biocompatible polymer powder with an aqueous medium to generate said paste. The paste comprising a biocompatible polymer may suitably be prepared in bulk and transferred/aliquoted into said second container.

In a preferred embodiment the container holding the paste comprising a biocompatible polymer is a medical delivery device suitable for dispensing flowable haemostatic compositions to a patient in need thereof, such as a syringe. In one embodiment, the second container is a single-use plastic syringe.

In one embodiment, the first and second containers are interconnectable. The connector portion may be a connector portion of a standard type, such as a Luer lock or Luer slip connector. The connector portion may be provided with a threaded portion for secure connection with matching connector. The dimensions of said Luer lock or Luer slip connection may be able to change the ability of mixing in air into the haemostatic composition during mixing of the dry thrombin composition and the paste comprising a biocompatible polymer. Further, the dimensions of the Luer lock or Luer slip connection may be able to influence the consistency of the haemostatic composition.

In one embodiment, the connector portion comprises a static mixer. The dimensions of said static mixer may be able to change the ability of mixing in air into the haemostatic composition during mixing of the dry thrombin composition and the paste comprising a biocompatible polymer. Further, the dimensions of the static mixer may be able to influence the consistency of the haemostatic composition.

Outer Package

In one embodiment the dry thrombin composition and/or the paste comprising a biocompatible polymer contained within e.g. a syringe, such as the herein disclosed syringe, or other containment unit, is further contained within an outer package so that the product is kept sterile until use. This will allow the user to remove the outer package and transfer the components of the haemostatic composition into a sterile field.

The outer package is usually made from a flexible, semi-rigid or rigid material and typically consists of materials such as plastic, aluminium foil and/or plastic laminate, where the plastic may be selected from the group consisting of PET, PETG, PE, LLDPE, CPP, PA, PETP, METPET, Tyvek and optionally bonded with an adhesive, such as polyurethane, or co-extruded.

In one embodiment, the outer package is an aluminium foil outer package.

The outer package preferably forms a complete barrier to moisture.

The outer package is preferably able to endure sterilisation treatment such as by radiation.

In one embodiment, the first syringe comprising a dry thrombin composition and the second syringe comprising a paste comprising a biocompatible polymer are contained in separate outer packages.

Sterilisation

The dry thrombin composition, the paste comprising a biocompatible polymer and/or the haemostatic composition of the present disclosure are preferably sterile. Any suitable sterilisation technique known in the art may be utilised. Sterilisation refers to any process that effectively kills or eliminates transmissible agents (such as fungi, bacteria, viruses, prions and spore forms etc.). Sterilisation can be achieved through e.g. application of heat, chemicals, and/or irradiation.

Sterilisation may be achieved by heat sterilisation, include autoclaving (uses steam at high temperatures) and dry heat.

Sterilisation may be achieved by irradiation, e.g. ionizing irradiation, so as to provide sterility to the components. Such irradiation may include e-beam (beta irradiation), X-rays, gamma and beta rays, UV light and subatomic particles. The level of irradiation and conditions for sterilisation, including the time, are those that provide sterile compositions. Sterilisation conditions are similar to those currently utilized in the art and can be determined by the skilled person.

Sterilisation may be performed by chemical sterilisation such as by using ethylene oxide gas, ozone, chlorine bleach, glutaraldehyde, formaldehyde, ortho phthalaldehyde, hydrogen peroxide and/or peracetic acid.

The dry thrombin composition is usually prepared using aseptic methods thereby providing a sterile dry thrombin composition in said first container.

In one embodiment, the surface of the first container comprising a dry thrombin composition is sterilised with chemical sterilisation, such as with ethylene oxide gas.

In one embodiment, the paste comprising a biocompatible polymer is sterilised by irradiation, such as by gamma irradiation.

In one embodiment, sterilisation of the second container comprising a paste comprising a biocompatible polymer is sterilised using beta or gamma irradiation, thereby providing a sterile paste and a sterile container.

In one embodiment sterilisation of the second container comprising a paste comprising a biocompatible polymer occurs as terminal sterilisation, i.e. when the second container comprising a paste comprising a biocompatible polymer is contained within an outer package.

Medical Use

The present disclosure further relates to use of the haemostatic composition obtained by the methods of this disclosure for promoting haemostasis and/or wound healing.

The haemostatic composition of the present disclosure may e.g. be used in an array of surgical procedures wherein bleeding control is desired. The haemostatic composition is in the form of a paste which conforms to irregular surfaces to stop bleeding fast and it is therefore useful for providing rapid haemostasis on rough or uneven surfaces where haemostatic sponges are not efficient.

In general, haemostatic pastes are prepared directly at the surgical site at the time of need by the medical practitioner, i.e. the doctors or nurses usually by addition of liquid (optionally comprising thrombin) to a container, such as a syringe, containing an amount of a biocompatible polymer. The biocompatible polymer may be pre-wetted with the liquid or be essentially dry (free-flowing powder). The paste is thus often prepared under extremely stressful conditions and it is therefore essential that the process for preparing the paste is simple and fast to ensure that the bleeding is arrested as quickly as possible and that no mistakes are made while preparing the paste such that the nurse can keep focus on the needs of the surgeon instead of on preparing the haemostat. It is also important that the consistency of the paste is suitable for use as a haemostatic paste and that the consistency of the product is independent from preparation to preparation and over time.

Currently available flowable paste products (Floseal® and Surgiflo®) require reconstitution of a thrombin composition in a liquid prior to mechanical mixing of said reconstituted thrombin solution with the biocompatible polymer by passing the biocompatible polymer and the liquid between two connected syringes a number of times to obtain a substantially homogenous paste. The reconstitution of the thrombin is time-consuming and error prone, two undesired factors in an OR setting. These products are often pre-prepared in the OR before surgery in case they are needed under surgery and unused product is often discarded causing unnecessary high OR costs.

The method of preparing a haemostatic composition of the present disclosure is superior to the currently available methods as it reduces number of handling steps in the procedure by allowing direct reconstitution of a dry thrombin composition in a paste. The haemostatic composition of the present disclosure may be prepared simply by adding an amount of a paste comprising a biocompatible polymer to a container comprising the dry thrombin composition and mixing the content, such as transferring the content between two interconnected syringes a number of times, whereupon a ready-to-use haemostatic paste comprising substantially homogenously distributed thrombin is formed.

The fact that no prior reconstitution of the dry thrombin composition in a liquid is required also means that less time is spent preparing the paste, which in turn leads to increased patient safety, both due to the fact that the haemostatic composition can be applied to the patient faster and that the simple preparation method decreases the likelihood of mistakes being made during the preparation of the haemostatic composition. Also, the method of preparing a haemostatic composition of the present disclosure can decrease OR costs as there is no need to pre-prepare the current product before surgery since preparation is so simple and fast.

Another notable advantage of the method of the present invention is that a kit consisting of fewer components can be prepared as compared to current haemostatic flowable kits. All there is required to prepare a flowable paste composition in the OR is the dry thrombin composition as described herein comprised within a first container, such as a syringe and a second container, such as a medical delivery device comprising a paste comprising a biocompatible polymer. Upon connection of the two and mixing, a ready-to-use flowable paste containing all necessary agents for effective haemostasis including thrombin is formed. Thus, no extra syringes, vial adapters, needles and mixing bowls are required with the product prepared according to the methods of the present disclosure. This means that the manufacturing costs can be decreased and also ensures good patient safety, since there are less components for the OR staff to keep track of during surgery. Needle-free preparation of the haemostat also ensures the safety of the OR staff.

In one embodiment the present disclosure relates to a method for arresting bleeding/promoting haemostasis in an individual in need thereof by application of the haemostatic composition prepared by the methods of the present disclosure to a site of bleeding.

The haemostatic composition of the present disclosure may be used for any type of surgery including general surgery, cardiothoracic surgery, vascular surgery, plastic surgery, paediatric surgery, colorectal surgery, transplant surgery, surgical oncology, trauma surgery, endocrine surgery, breast surgery, skin surgery, otolaryngology, gynaecology, oral and maxillofacial surgery, dental Surgery, orthopaedic surgery, neurosurgery, ophthalmology, podiatric surgery, urology.

In one embodiment the present disclosure relates to a method for promoting wound healing in an individual in need thereof by application of the haemostatic composition prepared by the methods of the present disclosure to the wound.

A "wound" refers broadly to injuries to the skin and/or underlying (subcutaneous) tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The present disclosure relates to treatment of any type of wound mentioned above using the haemostatic composition of the present disclosure.

The treatment of a wound can in principle result in healing of the wound or in accelerated healing of the wound. The accelerated healing can be a result of e.g. administration of a wound-healing promoting substance. Alternatively, the wound healing can be promoted by preventing bacterial or viral infection, or by reducing the risk of such an infection which would otherwise have prolonged the wound treatment process.

In one embodiment the present disclosure relates to a method for promoting bone and/or tendon healing in an individual in need thereof by application of the haemostatic composition prepared by the methods of the present disclosure to the injured bone/tendon.

The "individual" referred to herein may be any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In one embodiment the present disclosure relates to a haemostatic composition as disclosed herein, for use in the treatment of a wound, e.g. for arresting bleeding or for promoting wound healing.

A Haemostatic Kit

The present disclosure further relates to a haemostatic kit comprising the dry thrombin composition of the present disclosure and a paste comprising a biocompatible polymer matched to the amount of the dry thrombin composition so that upon mixing, a haemostatic composition having a thrombin content suitable for use in haemostasis will form.

Hence, in one embodiment the present disclosure relates to a haemostatic kit comprising:
a) a first syringe comprising a dry thrombin composition;
b) a second syringe comprising a paste comprising a biocompatible polymer; and
c) optionally an outer package, wherein the two syringes are interconnectable.

In one embodiment, the haemostatic kit comprises:
a) a first syringe comprising a dry thrombin composition in an outer package;
b) a second syringe comprising a paste comprising a biocompatible polymer in an outer package; and
c) optionally an outer package comprising the components of a) and b), wherein the two syringes are interconnectable.

In one embodiment, the kit further comprises one or more applicator tips.

The kit may optionally contain instructions for use of the kit.

The components of the haemostatic kit may be as described elsewhere herein.

EXAMPLES

Example 1: Thrombin Distribution in Paste

Materials:
2000 IU dry thrombin in a 10 mL glass syringe (first syringe).
5 mL of a gelatine paste in a 10 mL syringe (second syringe).
Method:
The two syringes are interconnected via a luer lock and the gelatine paste content is transferred to the syringe containing the dry thrombin composition (first transfer). The resulting mixture of thrombin and gelatine paste is then transferred back and forth between the first and the second syringes for a number of five times, resulting in a haemostatic composition contained in the second syringe (FIG. 1). The total number of transfers is 6 times. The haemostatic composition obtained is a flowable paste formulation comprising thrombin and is identified herein as the "6tomix" or "6TM" paste. As a consequence of mixing, a total of about 3 mL air is mixed into the paste providing a final volume of the paste of about 8 mL.

Results:
The final haemostatic composition is a paste having a volume of about 8 mL.

The thrombin content of the haemostatic composition is measured as the mean thrombin activity in different fractions of the haemostatic composition.

The following fractional divisions are applied: The start fraction (i.e. the first ⅓ haemostatic composition extruded from the syringe), the mid fraction (the middle ⅓ haemostatic composition extruded from the syringe) and the end fraction (the last ⅓ haemostatic composition extruded from the syringe).

The thrombin activity of the total haemostatic composition is set at 100% and the mean thrombin activity of the individual fractions is calculated as percentage of the total activity. A completely homogenous thrombin distribution in the haemostatic composition would result in a mean thrombin activity of each of the three fractions of 33.333%.

|  | Start fraction | Mid fraction | End fraction |
|---|---|---|---|
| Mean thrombin activity | 33% | 31% | 36% |

Variation in Thrombin Content:
The variation in thrombin content is calculated as the percentage difference in mean thrombin activity between two fractions.

The maximal variation in thrombin content is here calculated as follows:

$$(36/(31+36))-0.50)*100=3.7\%.$$

In conclusion, this demonstrates that a dry thrombin composition can be reconstituted directly in a gelatine paste, via six transfers of the two components between two syringes, to generate a haemostatic composition having a substantially homogenous distribution of thrombin in the haemostatic composition.

Example 2: Haemostatic Effect of Paste

Purpose
The purpose of the study was to test the haemostatic efficacy of the 6TM paste of Example 1. The haemostatic efficacy of the paste was compared to that of the commercially available Surgiflo® paste. Surgiflo® is a sterile, absorbable porcine gelatine paste formulation approved for haemostatic use by applying to a bleeding surface and is an established product in the market.

Haemostatic efficacy was tested in a porcine spleen biopsy model as described below.

Experimental Model
A porcine spleen biopsy-punch model was used applying 8 mm punctures (3 mm deep) in the spleen with an initial compression period of 10 seconds followed by an evaluation period of 120 seconds and following compression periods of 10 seconds.

The porcine spleen biopsy-punch model is an established model for evaluating haemostatic efficacy of haemostatic pastes in vivo (Hutchinson et al., 2015, Surgical Technology International XXVII). The porcine spleen biopsy-punch model of the present study is similar to the one used in Hutchinson et al., 2015. The present study was conducted with permission from the The Animal Experiments Inspectorate of Denmark (Dyreforsogstilsynet).

Experimental Animal

The pig is the animal of choice for this model since it has a large volume of blood (70 ml/kg) and a large vascular spleen that enables many haemostatic comparisons in a single animal. The female pigs of the present study had an approximate weight of 40 kg (±5 kg) and an approximate age of three months. The inclusion criterion for the pig was the weight. The lower weight limit was set to ensure that the organs to be tested were of an appropriate size, while the upper limit was a guidance to ensure that the size of the pig was standardized.

At the time of surgery, the tested pigs showed no signs of clinical illness.

Anaesthesia and Fluid Therapy

The pigs had been fasting for at least 6 hours before surgery. The anaesthesia was induced by an intramuscular injection (1 mL/10 kg) of the following mixture: 6.25 mL Narcoxyl (Xylazin 20 mg/mL), 1.25 mL Ketaminol (Ketamin 100 mg/mL), 2 mL Turbogesic (Butorphanol 10 mg/mL), and 2 mL Metadon (Methadone 10 mg/mL) added to a vial of Zoletil 50 Vet (containing 125 mg Tiletamine and 125 mg Zolazepam).

The pigs were intubated and ventilated with a respirator with a mixture of 0.5 L oxygen/2.5 L air/min. The anaesthesia was maintained by intravenous administration of Fentanyl (50 µg/mL, 1 mL/10 kg/hour) and Propofol (10 mg/mL, 1.5 mL/kg/hour). The animals were kept normohydrated with Lactated Ringer's solution (125 mL/hour). It has previously been evaluated that the use of the mentioned medication does not affect haemostasis.

The pigs used in the present study were euthanized following surgery using an overdose of barbiturate resulting in cardiac arrest.

Test Procedure
Sample Preparation

The 6TM paste of the present invention was prepared as described in Example 1, i.e. by mixing a wet gelatine paste with a dry preparation of thrombin without prior reconstitution of the thrombin in saline.

The Surgiflo paste (control) was mixed with a thrombin solution according to the Surgiflo Instructions for Use dated 11 Jun. 2014.

Once mixed with thrombin, the chemical composition and water content of the control product (Surgiflo) and the 6TM paste of the present invention was the same.

To mimic storage conditions, the pastes were stored at 40° C. for 3 months prior to mixing with thrombin and subsequent testing, the only difference being that the control paste contained 2 ml less liquid (saline) than the 6TM paste of the present invention during storage. The 2 ml saline with thrombin were added to the control paste immediately prior to testing whereas the 6TM paste of the present invention was mixed with dry thrombin as described in Example 1 immediately prior to testing.

Surgical Procedures

A midline abdominal incision was made to expose the spleen. An 8 mm punch (3 mm deep) was made in the spleen. The bleeding intensity was evaluated on a scale from 0-5 as described herein below. Only bleeding intensities 3 and 4 were regarded as acceptable. The punch was now ready for either a control sample or a test sample. A new punch was made for every test sample.

Each sample type was tested 7 times (n=7). The samples were tested in a randomized order.

A 12 minute negative control, using only wetted gauze, was performed at the initiation and completion of the testing period on each pig. The negative controls were used as an indication of the animal's ability to bleed throughout the study.

The primary test parameter was to measure the time to haemostasis (TTH). TTH is defined as the total time minus the final haemostasis evaluation period ensuring that no further bleeding occurred, i.e. no re-bleed.

The evaluation of bleeding intensity and the application of test samples and negative controls are described in detail below.

Bleeding Intensity

The bleeding intensity of each punch was evaluated by the surgeon on a scale from 0-5 (see Table below).

Bleeding intensity was noted at t=0 for each punch. Only tests performed on wounds with bleeding intensity of 3-4 were used for further analysis.

TABLE

| Bleeding intensity levels | |
|---|---|
| Level 0 | No bleeding (for at least 30 seconds) |
| Level 1 | No bleeding observed initially, bleeding observed within the first 30 seconds of injury |
| Level 2 | Bleeding observed immediately following injury, wound site fills in approximately 30 seconds |
| Level 3 | Bleeding observed immediately following injury, wound site fills in approximately 3 seconds |
| Level 4 | Bleeding observed immediately following injury, wound site fills immediately following injury (does not include arterial or pulsating bleeding) |
| Level 5 | Bleeding observed immediately following injury, wound site fills immediately following injury (including arterial or pulsating bleeding) |

Negative Control

Wetted gauze was placed directly on the punch. Digital pressure was applied for 30 seconds followed by a 120 second haemostasis evaluation period. Haemostasis was evaluated (defined as no sieving of blood from under test article for 30 seconds). If haemostasis was not achieved within the 120 seconds, additional 30 seconds digital pressure was applied and a 120 second re-evaluation for haemostasis was performed. Tamponade application and observation periods were performed until bleeding stopped, and haemostasis achieved, or until the testing period reached 12 minutes. Haemostasis was not achieved within the 12 minutes testing period for the negative controls, thus showing the ability of the pig to bleed throughout the study.

Application of Test Samples

Approximately 1-2 mL paste was applied directly into the punch with an applicator tip. During application the tip penetrated into the punch to ensure tissue contact. After application gauze wetted in 0.9% saline was placed on the punch. Digital pressure (tamponade) was applied for 10 seconds. The pressure was stopped and the gauze removed followed by evaluation of haemostasis. If no sieving of blood was seen from under the test article for 120 seconds, it was concluded that haemostasis was achieved and the experiment is ended. If blood sieved from under the test article in the 120 second time frame, the time for sieving was recorded and digital pressure was again applied for 10 seconds, after which haemostasis was inspected. This procedure was continued until haemostasis was achieved or for 12 minutes, whichever came first.

Calculation Example for Evaluation of Time to Haemostasis 10 seconds of digital pressure, inspect for haemostasis: blood sieves after 39 seconds, digital pressure for another 10 seconds, inspect for haemostasis for 120 seconds: no sieving—conclusion: haemostasis was achieved after 10+39+10 seconds=59 sec. i.e. the last observation period is not included in calculating the TTH.

Results

Figure 3:
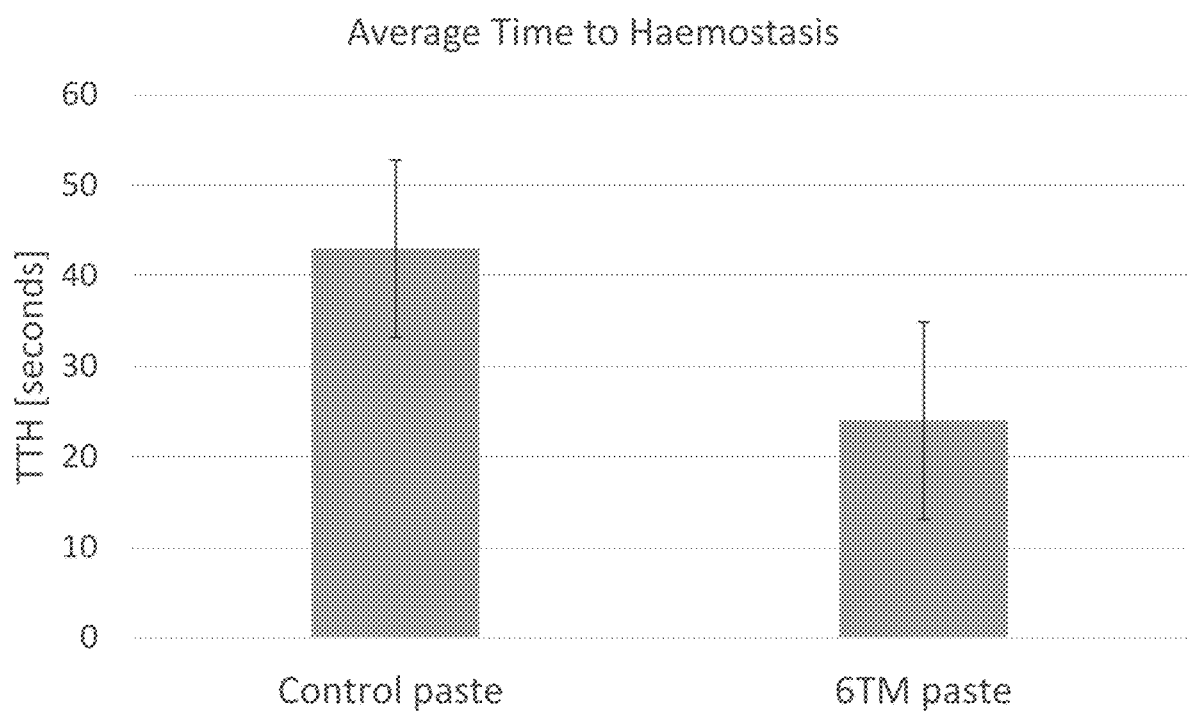

The results of the present study are shown in the table below and further depicted in FIG. 3.

| Measure | Control paste (n = 7) | 6TM paste (n = 7) |
|---|---|---|
| Time to Haemostasis (TTH) mean ± SEM* | 43 ± 9.8 s | 24 ± 10.9 s |

*SEM: Standard error of the mean.
"s" is seconds

The results show an almost 2-fold reduction in the mean TTH of the 6TM paste as compared to the control paste.

The median TTH of the control paste was 37 seconds, while the median TTH of the 6TM paste was 10 seconds.

The data surprisingly shows that the 6TM paste prepared according to the present invention leads to haemostasis faster and more consistently than the control paste.

The invention claimed is:

1. A method of preparing a haemostatic composition, the method comprising:
    a) providing a dry thrombin composition in a first syringe;
    b) providing a paste comprising a biocompatible polymer in a second syringe wherein the paste comprises the biocompatible polymer in a content of 7% w/w to 20% w/w;
    c) connecting the first syringe and the second syringe using a suitable connector; and
    d) mixing the contents of the syringes by transferring the contents between the syringes for 5 to 10 times, to produce a haemostatic composition having a homogenous distribution of thrombin and having a variation in thrombin content throughout the haemostatic composition of less than 20%.

2. The method according to claim 1, wherein the homogenous distribution of thrombin is characterized by a variation in thrombin content throughout the haemostatic composition of less than 10%.

3. The method according to claim 1, wherein the haemostatic composition is a paste suitable for use in haemostasis and/or wound healing.

4. The method according to claim 1, wherein the haemostatic composition is a flowable composition.

5. The method according to claim 1, wherein the dry thrombin composition is prepared by spray-drying or freeze-drying.

6. The method according to claim 1, wherein the biocompatible polymer consists of powder particles which are substantially insoluble in an aqueous medium.

7. The method according to claim 1, wherein the biocompatible polymer is cross-linked.

8. The method according to claim 1, wherein the biocompatible polymer is gelatine, collagen, chitin, chitosan, alginate, cellulose, oxidised cellulose, polyglycolic acid, or polyacetic acid, or combinations thereof.

9. The method according to claim 1, wherein the biocompatible polymer comprises or consists of gelatine.

10. The method according to claim 1 wherein the haemostatic composition comprises one or more hydrophilic compound(s).

11. The method according to claim 1, wherein the haemostatic composition comprises one or more further bioactive agents capable of stimulating haemostasis, wound healing, bone healing, tissue healing and/or tendon healing.

12. The method according to claim 1, wherein the haemostatic composition further comprises one or more extrusion enhancer(s).

13. The method according to claim 1, wherein the first syringe is a glass syringe or wherein the first syringe comprises a glass insert comprising the dry thrombin composition.

14. A kit comprising:
    a) a first syringe comprising a dry thrombin composition;
    b) a second syringe comprising a paste comprising a biocompatible polymer, wherein the paste comprises the biocompatible polymer in a content of 7% w/w to 20% w/w;
    c) optionally an outer package, and
    d) instructions for using the kit for preparing a haemostatic composition wherein the two syringes are interconnectable to allow for transferring the contents between the syringes for 5 to 10 times, to produce a haemostatic composition having a homogenous distribution of thrombin and having a variation in thrombin content throughout the haemostatic composition of less than 20%.

15. A method for reconstituting a dry thrombin composition, the method comprising:
    a) providing a dry thrombin composition in a first syringe;
    b) providing a paste comprising a biocompatible polymer in a second syringe, wherein the paste comprises the biocompatible polymer in a content of 7% w/w to 20% w/w;
    c) connecting the first syringe and the second syringe using a suitable connector; and
    d) mixing the contents of the syringes by transferring the contents between the syringes for 5 to 10 times, to produce a haemostatic composition having a homogenous distribution of reconstituted thrombin and having a variation in thrombin content throughout the haemostatic composition of less than 20%.

16. The method according to claim 1, wherein the number of transfers is between 6 and 10 times.

17. The method according to claim 1, wherein the thrombin concentration in the haemostatic composition is in the range of 50 IU/mL to 1000 IU/mL.

18. A method of preparing a haemostatic composition, the method comprising:
    a) providing a dry thrombin composition in a first syringe;
    b) providing a gelatin paste in a second syringe, wherein the paste comprises gelatin in a content of 7% w/w to 20% w/w;
    c) connecting the first syringe and the second syringe using a suitable connector; and
    d) mixing the contents of the syringes by transferring the contents between the syringes for 5 to 10 times, to produce a haemostatic composition having a homogenous distribution of thrombin and having a variation in thrombin content throughout the haemostatic composition of less than 20%.

* * * * *